United States Patent
Stern

(10) Patent No.: US 7,282,223 B2
(45) Date of Patent: Oct. 16, 2007

(54) NUTRITIONAL DIETARY KIT FOR USE IN PREPARING AN INDIVIDUAL FOR GASTROINTESTINAL PROCEDURE

(75) Inventor: Howard S. Stern, Old Westbury, NY (US)

(73) Assignee: E-Z-EM, Inc., Lake Success, NY (US)

( * ) Notice: Subject to any disclaimer, the term of this patent is extended or adjusted under 35 U.S.C. 154(b) by 137 days.

(21) Appl. No.: 10/916,047

(22) Filed: Aug. 10, 2004

(65) Prior Publication Data

US 2005/0112178 A1    May 26, 2005

Related U.S. Application Data

(63) Continuation of application No. 10/177,276, filed on Jun. 21, 2002, now Pat. No. 6,866,873, which is a continuation-in-part of application No. PCT/US01/32039, filed on Oct. 12, 2001.

(60) Provisional application No. 60/240,569, filed on Oct. 13, 2000.

(51) Int. Cl.
*A61K 36/00* (2006.01)
*A61K 31/74* (2006.01)
*A23L 1/30* (2006.01)
*A23L 1/31* (2006.01)

(52) U.S. Cl. .................. 424/725; 424/78.01; 426/531; 426/615; 426/641; 426/648; 426/800; 435/810

(58) Field of Classification Search ............... None
See application file for complete search history.

(56) References Cited

U.S. PATENT DOCUMENTS

| | | |
|---|---|---|
| 4,565,702 A | 1/1986 | Morley et al. |
| 4,765,994 A | 8/1988 | Holmgren et al. |
| 5,472,952 A | 12/1995 | Smidt et al. |
| 5,545,414 A | 8/1996 | Behr et al. |
| RE36,288 E * | 8/1999 | Lin et al. ............ 514/52 |
| 5,985,339 A * | 11/1999 | Kamarei ............ 426/72 |
| 6,287,609 B1 | 9/2001 | Marlett et al. |
| 6,428,320 B1 * | 8/2002 | Archuleta et al. ....... 434/127 |
| 6,436,036 B1 * | 8/2002 | Miller-Kovach et al. ... 600/300 |
| 6,548,043 B1 * | 4/2003 | Wagner et al. ............ 424/1.81 |
| 2001/0002269 A1 | 5/2001 | Zhao |
| 2005/0175542 A1 * | 8/2005 | Lefere et al. ............ 424/9.41 |

FOREIGN PATENT DOCUMENTS

| | | |
|---|---|---|
| EP | 0 396 165 A | 11/1990 |
| EP | 0 423 771 A | 4/1991 |
| JP | 11 343251 A | 12/1999 |
| WO | WO97/07689 A1 | 3/1997 |

OTHER PUBLICATIONS

Internet document from a 1997 Brochure entitled 'Dubuque Internal Medicine', 5 pages, downloaded from internet on Sep. 17, 2003.*
Heber et al. 1994. J Am. College Nutr. vol. 13, No. 6, pp. 608-614.*
Ditschuneit et al. 1999. Am. J. Clin. Nutr. vol. 69, pp. 198-204.*
Chemitsky, L. 1999 Internet article entitled Slim-Fast and Weight Loss, 10 pages, downloaded from internet on Mar. 30, 2006.*
Internet article entitled Go Ask Alice —Slim Fast, originally published Feb. 24, 1995, 2 pages, downloaded from internet on Mar. 30, 2006.*
Internet article entitled 'Nutrition', 6 pages, downloaded from internet on Mar. 30, 2006.*
Supplementary European Search Report from corresponding European Application No. EP 01 97 9784 dated Feb. 3, 2005.

* cited by examiner

*Primary Examiner*—Christopher R. Tate
(74) *Attorney, Agent, or Firm*—Alston & Bird LLP

(57) ABSTRACT

This invention relates to a nutritional kit for use in preparing an individual for a predetermined activity which requires a clean digestive tract, particularly the colon. Such predetermined activities include, but are not limited to, gastrointestinal surgery and colon screenings. Specifically, the present invention provides an individual low amounts of fat, dietary fiber and solid food content to minimize stool formation and/or facilitate removal of stool from the digestive tract prior to the predetermined activity. The present invention also provides the individual with sufficient calories and nutrition to enable the individual to conduct daily, routine activities while utilizing the present invention. In one alternative embodiment, the present kit provides a variety of pre-packaged, ready to eat or easy to prepare nutritional liquid or solid foods which when coordinated with a laxative regimen, result in removal of residue such that a medically and/or diagnostically useful procedure can be performed on the digestive tract.

18 Claims, 19 Drawing Sheets

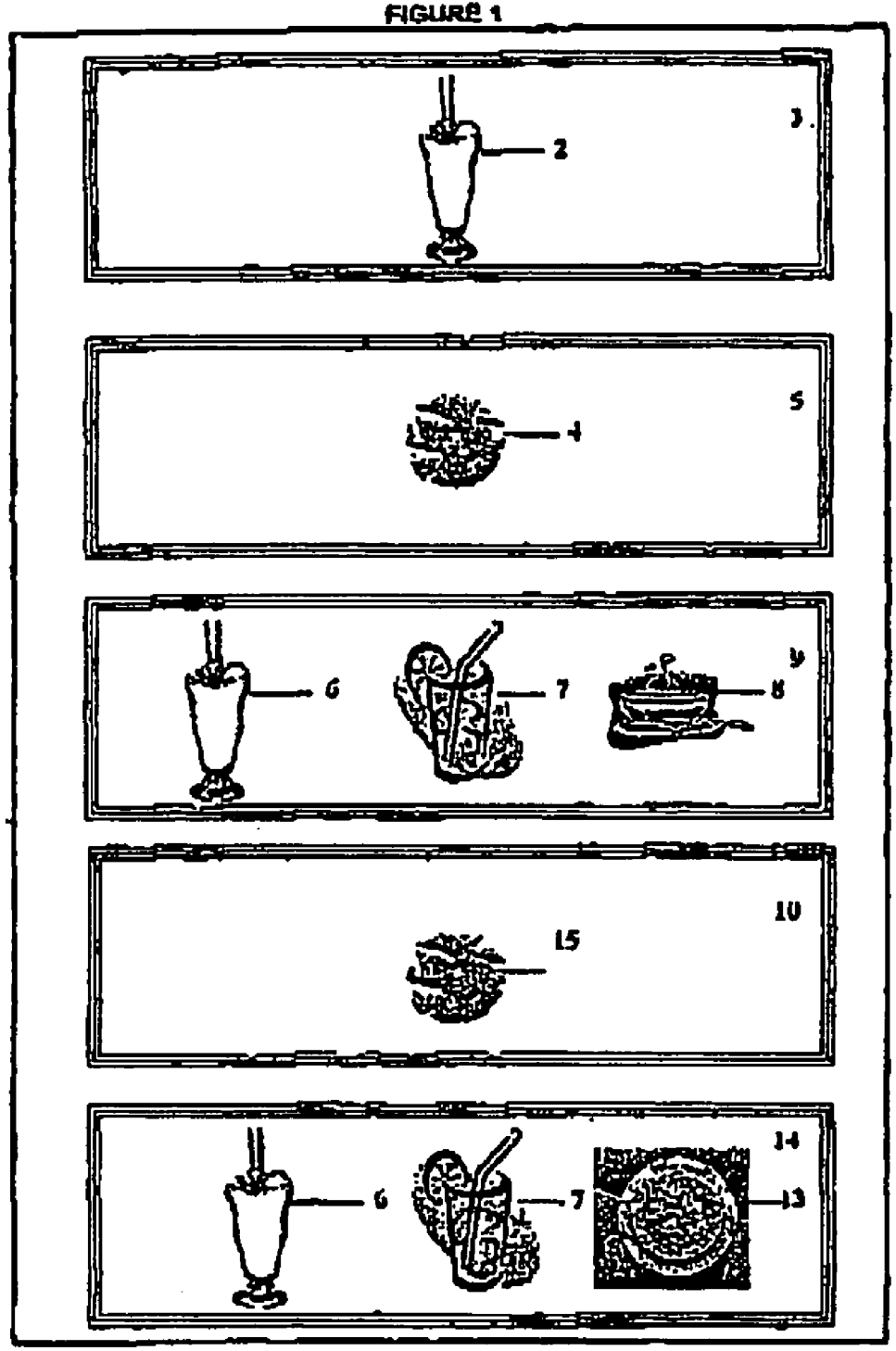

FIGURE 2

Please place a "✓" next to the items you ate for meals:   15

BREAKFAST                                    LUNCH

☐   Vanilla Nutritional Shake          ☐   Vanilla Nutritional Shake

☐   Lemon Drink

☐   Chicken Noodle Soup

BETWEEN MEALS                                DINNER

☐   Potato Poppers                      ☐   Vanilla Nutritional Shake

☐   Chocolate Flavored Energy Bar       ☐   Lemon Drink

☐   Chocolate Flavored Energy Bar       ☐   Stroganoff

☐   Cinnamon Apple Sauce

After Dinner no food.

FIGURE 6
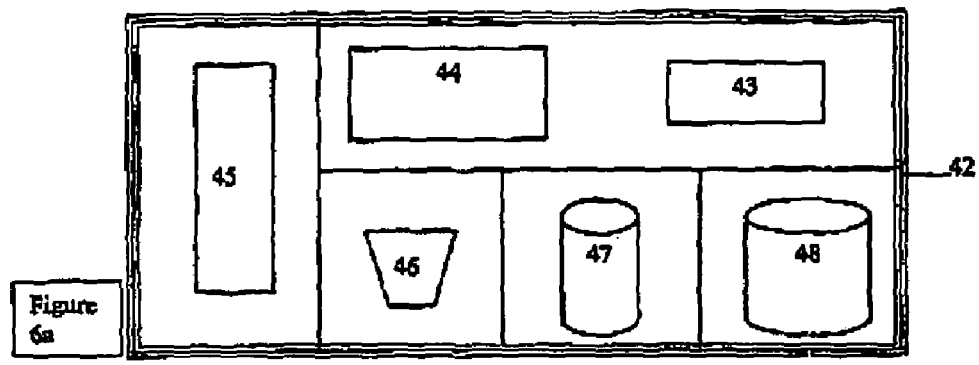
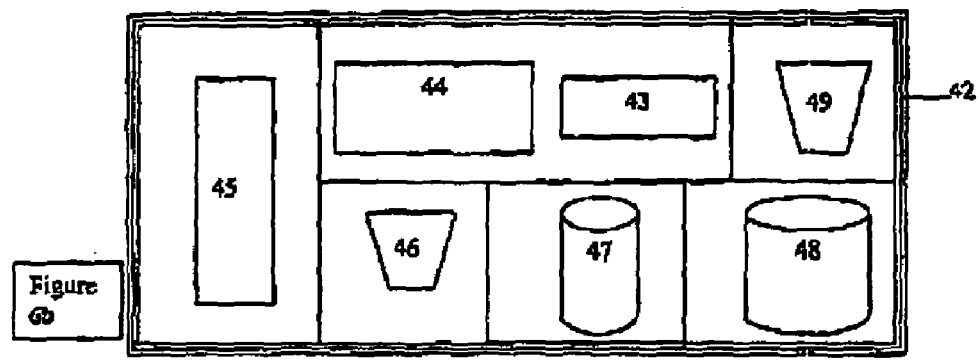
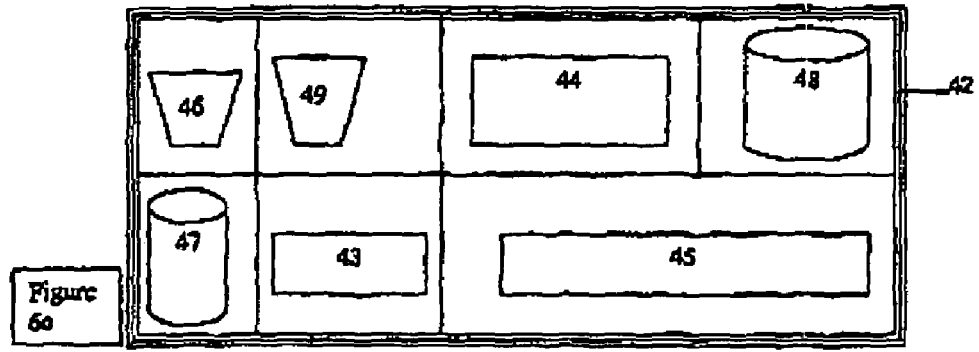

FIGURE 7
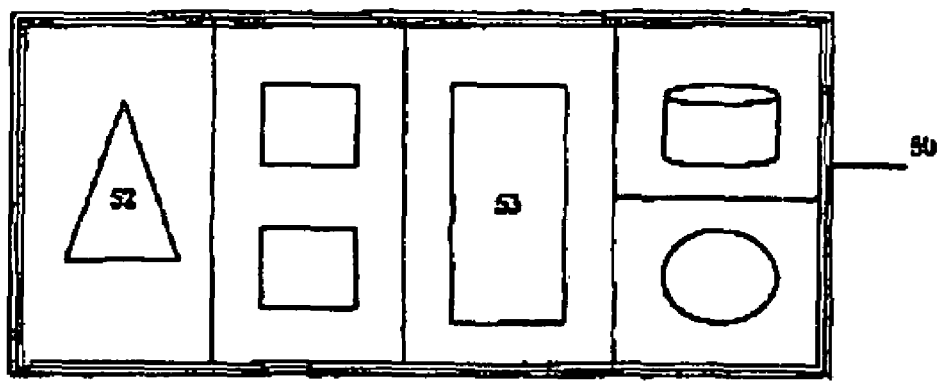
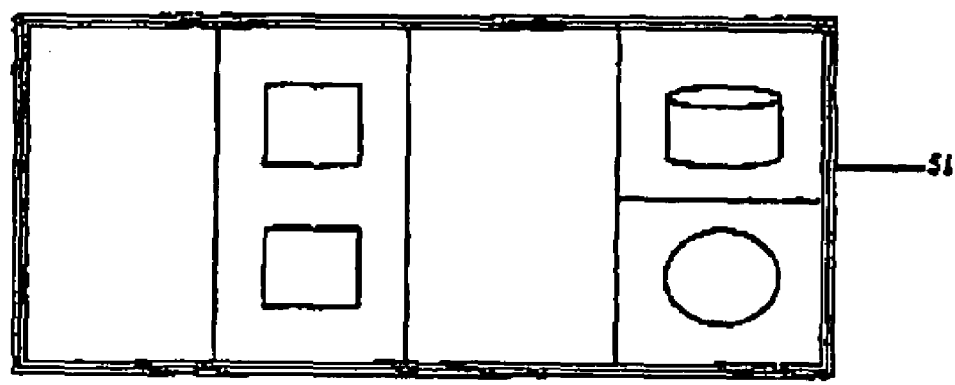
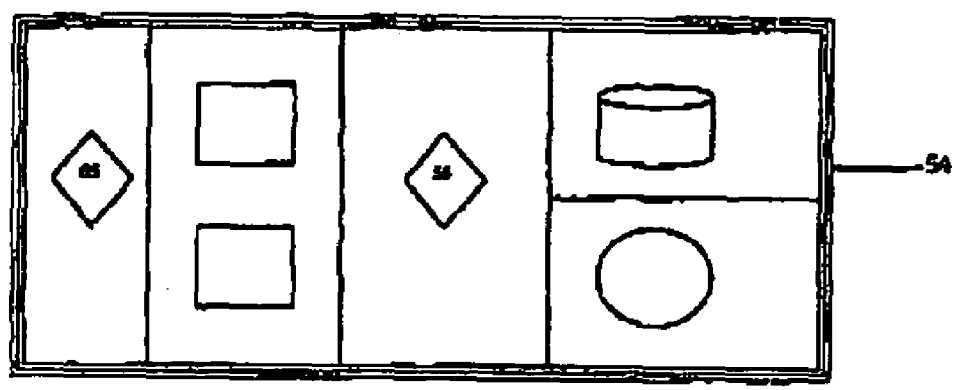

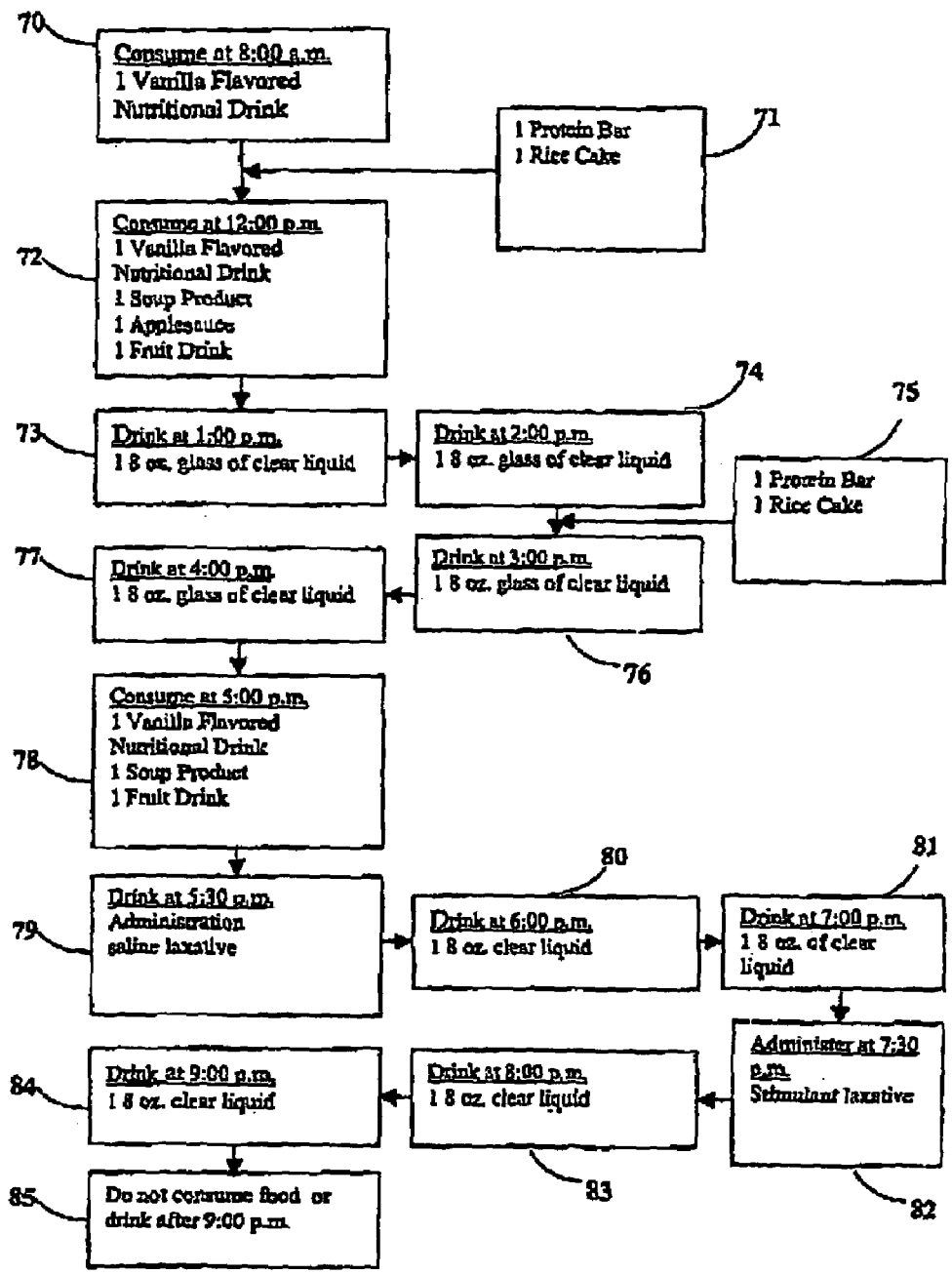

FIGURE 11

The day before the colonoscopy:

1. You may have only clear liquids to eat or drink. This includes liquids that you can see through such as apple juice, jello, white grape juice, bouillon, coffee, tea. DO NOT drink or eat any diary products, carbonated drinks, red jello, or juices with pulp like orange juice (may drink strained orange juice). Please drink lots of fluids the day before the test.

2. Please take your usual medications as prescribed.

3. Purchase Fleet™ PhospoSoda from your local drug store (3 oz)
   a) Mix 1-½ oz in 4 oz of water at 4PM and drink
   b) Mix 1-½ oz in 4 oz of water at 8PM and drink The day of the examination:

1. Do not eat or drink anything except a few sips of water. If your test is in the afternoon, you may have a clear liquid breakfast at 8AM.

2. If you are a diabetic requiring insulin injections, take ½ the amount you usually take, if you take any Regular Insulin do not take it.

3. If you are taking medicine by mouth, take your usual dose. Bring all medicine you are taking with you to the exam.

FIGURE 12

Contents of Kit A:

3 – Vanilla Nutritional Drink Mix
1 – Mixing container with cover
1 – 4 oz. Apple Sauce
2 – Fruit Drink Mix
2 – Soup Mix
- Chicken Noodle
- Clear Broth
1 – Hot Cup (for Broth)
1 – Package of Carmel Rice Cakes
2 – Nutrition Bar
1 – LoSo Prep™ Bowel Cleansing System

FIGURE 13

Contents of Kit B:

3 – Vanilla Nutritional Drink Mix
1 – Mixing container with cover
1 – 4 oz. Apple Sauce
2 – Fruit Drink Mix
2 – Soup Mix
 - 1 Chicken Noodle
 - 1 Clear Broth
1 – Hot Cup (for Broth)
1 - LoSo Prep™ Bowel Cleansing System

FIGURE 14

LOW RESIDUE NUTRITONAL PROTOCOL

This diet is to be used in preparation for gastrointestinal testing that requires evacuation of the bowel after digestion.
This diet controls fat intake with foods that are known to decrease fecal output.

Special Notes

Milk products (e.g. whole milk, skim milk, cheese, yogurt) are limited to only two (2) cups, two days before the exam. DO NOT drink or eat any milk products on either the day before the exam or the day of the exam.

Fatty foods slow the emptying process and defeat the goal of bowel preparation. In order to prevent this from happening, please pay very close attention to the suggested menu on the next page ("2 DAYS BEFORE THE EXAM").

Caffeinated drinks (e.g., coffee, tea, caffeinated cola beverages, chocolate drinks) can dehydrate you. These should be avoided since the goal of this preparation is to keep you well hydrated.

Therefore, do not drink any caffeine containing beverages on the day before the exam. You may however drink decaffeinated beverages (e.g. decaffeinated coffee, decaffeinated cola beverages) during this time period.

LoSo Prep™ – Bowel Cleansing System

Mixing the Magnesium Citrate Effervescent laxative ahead of time will allow for proper mixing. Refrigerating the mixture may make it taste better.

If the suppository feels soft to the touch, it may be refrigerated for one hour, prior to insertion in order to firm it up.

FIGURE 15

DAY 1
(2 DAYS BEFORE THE EXAM)
Suggested menu for two (2) days before the exam
*START WITH LUNCH*

Please place a "✓" next to the items you ate for these meals:

| LUNCH | DINNER |
|---|---|
| Soup ___ | Soup ___ |
| fish/white meat chicken ___ | fish/white meat chicken ___ |
| white rice ___ | white rice ___ |
| bread crackers ___ | bread cracker ___ |
| dessert/fruit ___ | dessert/fruit ___ |

| | ALLOWED | PLEASE AVOID |
|---|---|---|
| Dairy: | limit 2 cups use low fat products; milk, plain yogurt | yogurt with fruit skins or seeds; strongly flavored cheeses |
| Meat: | plainly prepared; fish, poultry, eggs | added fats, gravies, fried sauces, heavy seasonings, peanut butter |
| Potato/Substitutes: | white rice, spaghetti, noodles, macaroni, potato with no skin | potato with skin, brown rice |
| Bread/Cereal: | white (refined) breads Saltine crackers, cooked rice | whole grain (graham, bran, cornmeal) breads, corn crackers & cereals, popcorn |
| Fruit/Fruit Juices: | clear fruit juices, canned fruit (No seeds, skin or membranes) | raw fruits, raisins, dried fruits, prunes/prune juice, skins |
| Beverages: | coffee (limited), fruit flavored drinks, tea, carbonated drinks | all others |
| Soup: | Bouillon/broth, strained soups, soups made with allowed vegetables & meats | all others |
| Desserts: | gelatin, fruit ice/popsicle | custards, nuts, seeds, hard clear candies, fruits that are not allowed on this list |
| Miscellaneous: | salt, pepper, jelly, sugar, honey, syrup | cloves, garlic, seed spices, chili sauce, barbeque sauce, any strongly flavored spice or sauce, mustard, jam |

FIGURE 16
Kit A
DAY 2
(THE DAY BEFORE THE EXAM)

YOU MUST DRINK AT LEAST TWO (2) QUARTS OF WATER\*
BETWEEN THE HOURS OF 1:00 pm AND 10:00 pm

Please place a "✓" next to the items you have eaten at each meal, and any fluid you may have drunk:

BREAKFAST

☐ Vanilla Drink Mix\*\*

LUNCH

☐ Fruit Drink Mix
☐ Chicken Noodle Soup
☐ Vanilla Drink Mix\*\*
☐ Applesauce

DINNER – 5:00 pm

☐ Fruit Drink Mix
☐ Soup – Clear Broth
☐ Vanilla Drink Mix\*\*

BETWEEN MEALS

☐ Caramel Rice Cakes
☐ Nutrition Bars

FLUID INTAKE MINIMUM

| | |
|---|---|
| ☐ 1:00 pm | 1 full 8 oz. glass of water\* |
| ☐ 2:00 pm | 1 full 8 oz. glass of water\* |
| ☐ 3:00 pm | 1 full 8 oz. glass of water\* |
| ☐ 4:00 pm | 1 full 8 oz. glass of water\* |

\*clear apple juice, or iced tea (decaffeinated), plain, or flavored club soda may be substituted.

\*\*Place the contents of the Vanilla Drink Mix in the provided mixing container. Add 8 oz. of cold water. Cover the container and shake vigorously. Let stand for two (2) minutes. Shake vigorously again. Drink the entire contents.

FIGURE 17
Kit B

---

DAY 2
(THE DAY BEFORE THE EXAM)

**YOU MUST DRINK *AT LEAST* TWO (2) QUARTS OF WATER\***
BETWEEN THE HOURS OF 1:00 pm AND 10:00 pm

Please place a "√" next to the items you have eaten at each meal, and any fluid you may have drank:

BREAKFAST

☐ Vanilla Drink Mix\*\*

LUNCH

☐ Fruit Drink Mix
☐ Chicken Noodle Soup
☐ Vanilla Drink Mix\*\*
☐ Applesauce

DINNER – 5:00 pm

☐ Fruit Drink Mix
☐ Soup – Clear Broth
☐ Vanilla Drink Mix\*\*

FLUID INTAKE MINIMUM

☐ 1:00 pm　　　　　1 full 8 oz. glass of water\*
☐ 2:00 pm　　　　　1 full 8 oz. glass of water\*
☐ 3:00 pm　　　　　1 full 8 oz. glass of water\*
☐ 4:00 pm　　　　　1 full 8 oz. glass of water\*

\*clear apple juice, or iced tea (decaffeinated), plain, or flavored club soda may be substituted \*\*Place the contents of the Vanilla Drink Mix in the provided mixing container. Add 8 oz. of cold water. Cover the container and shake vigorously. Let stand for two (2) minutes. Shake vigorously again. Drink the entire contents.

FIGURE 18

AFTER DINNER – 5:30 pm

Please place a "✓" next to the items after you have finished that portion of the prep.

- After dinner, wait about one half hour prior to beginning your prep with the provided Bowel Cleansing System and taking the Magnesium Citrate.
- Do not eat any solid foods after your specified dinner and before taking the Magnesium Citrate.
- Completion of this step at or prior to 6:00 pm will allow completion of the laxation process to occur prior to bed-time (10:00 pm).

Follow these instructions:

- Mix the Magnesium Citrate Effervescent laxative. Allow the contents to effervesce (fizz) for a minimum of fifteen (15) minutes.
- Drinking the Magnesium Citrate mixture chilled will help to enhance the flavor.
- ☐ Drink the entire contents of the glass.

**\*\*IMPORTANT NOTE\*\***

You will feel an urge to move your bowels within one (1) hour or not later than 7 hours after drinking the Magnesium Citrate. It is important that you be near a toilet.

After drinking the Magnesium Citrate it is very important that you drink fluids in order to re-hydrate yourself. It is recommended that you adhere to the following schedule:

- ☐ 6:00 pm — 1 full 8 oz. glass of water\*
- ☐ 7:00 pm — 1 full 8 oz. glass of water\*

\*clear apple juice, or iced tea (decaffeinated), plain, or flavored club soda may be substituted ☐ 7:30 pm – Take the four (4) Bisacodyl Tablets

- Peel the backing off the Bisacodyl Tablet packaging
- Remove all four (4) enclosed tablets
- Take all four of them with one (1) full 8 oz. glass of water.

**\*\*DO NOT CHEW THE TABLETS\*\***

**\*\*IMPORTANT NOTES\*\***

- The Bisacodyl tablets are to be taken two (2) hours after taking the Magnesium Citrate Effervescent laxative.
- DO NOT give to children under the age of six (6) years of age, or to persons who cannot swallow them without chewing, unless directed by a doctor.
- DO NOT take tablets within one (1) hour after taking an antacid tablet and/or milk.
- This product will generally produce a bowel movement within six (6) to twelve (12) hours.

- ☐ 8:00 pm — 1 full 8 oz. glass of water\*
- ☐ 9:00 pm — 1 full 8 oz. glass of water\*

\*or clear apple juice, or iced tea (decaffeinated), plain, or flavored club soda may be substituted.

DAY 0
(THE DAY OF THE EXAM)

Upon waking, please follow these instructions for the administration of the suppository.

- Remove the suppository from the foil wrapper.

<u>NOTE</u>: If the suppository feels soft to the touch while in the foil wrapper, it may be refrigerated for up to one (1) hour, prior to insertion, in order to firm it up.

- In the presence of anal fissures or hemorrhoids, the suppository may be coated to the tip with petroleum jelly before insertion.

☐ Lie on your side and, with the pointed end first, push the suppository high into the rectum so that it will not slip out.

- Try to retain the suppository for at least 15 to 20 minutes.

- If you feel the suppository must come out immediately, it was not inserted high enough into the rectum, and should be inserted even further.

- Allow up to 6 - 120 minutes for complete evacuation of the colon <u>prior to departure</u> to appointment.

NUTRITIONAL DIETARY KIT FOR USE IN PREPARING AN INDIVIDUAL FOR GASTROINTESTINAL PROCEDURE

CROSS REFERENCE TO RELATED APPLICATIONS

This is a continuation of U.S. application Ser. No. 10/177,276, filed Jun. 21, 2002, now U.S. Pat. No. 6,866,873 which is a continuation-in-part of International Application No. PCT/US01/32039, with an international filing date of Oct. 12, 2002, published in English under PCT Article 21(2) under publication No. WO 02/30439. The International Application claims priority under 35 U.S.C. Section 119(e) from U.S. Provisional Application Ser. No. 60/240,569, filed Oct. 13, 2000. Each of these prior applications and the international publication are incorporated herein by reference in their entirety.

FIELD OF THE INVENTION

This invention relates to a nutritional dietary system, formulation, kit and method for use in preparing an individual for a predetermined activity. Specifically, the present invention provides an individual low amounts of fat, dietary fiber and solid food content to aid in the minimization in and/or removal of food residue from the digestive tract. The present invention also provides the individual with sufficient calories and nutrition to enable the individual to conduct daily, routine activities while utilizing the present invention. In one alternative embodiment, the nutritional dietary regimen of the present invention is used to minimize the production of and/or facilitate the removal of food residue from the digestive tract in an individual preparing for a predetermined medical activity, such as a medical or diagnostic procedure, including gastrointestinal surgery or colon screening and the like. In another alternative embodiment, the dietary regimen of the present invention provides a variety of pre-packaged, ready to eat or easy to prepare nutritional liquid or solid foods which, when coordinated with a laxative regimen, result in removal of food residue such that a medically and/or diagnostically useful procedure can be performed on the digestive tract.

BACKGROUND OF THE INVENTION

The digestive tract is a major component of the gastrointestinal system. Essentially, it is a tube about five meters in length of variable cross-sectional areas running from mouth to anus that includes the mouth, pharynx, esophagus, stomach, small intestine, large intestine, which includes the colon, also known as the bowel. In the digestive tract, food is propelled by muscular contractions through its different regions. These contractions are referred to as peristalsis. Eventually, unabsorbed food residues are moved to the end of the tract and are eliminated from the body in the form of solids, semi-solids or liquids.

As used herein the term "digestive tract" includes, but is not limited to, the mouth, pharynx, esophagus, stomach, small intestine and large intestine. Also, as used herein, the terms "food residue" and "residue" include any composition of matter resulting from digested food and which has not been absorbed by the body's digestive system, including, but not limited to, any solid, semi-solid or liquid matter in the digestive tract. Such food residue includes, but is not limited to, any solid, semi-solid or liquid stool matter.

A digestive tract substantially free of food residue may be desirable, or even necessary, for a variety of medical reasons. For example, it is often preferable for an individual to undergo surgery with an empty stomach, or with a stomach containing little or no solid matter, because anesthesia or medication given to the patient prior to, during, or after surgery may cause the patient to vomit. Vomiting may pose a health danger if solid particles from the vomit are aspirated.

A substantially or completely residue-free digestive tract may also be desirable or necessary for surgery on any part of the gastrointestinal system, including, for example, surgery on the colon, abdomen, esophagus, stomach, duodenum, liver, pancreas, intestines, rectum and anus. Gastrointestinal surgery may be necessary to treat, for example, diseases such as colon cancer, rectal cancer, Crohn's disease, ulcerative colitis and diverticulitis.

If the digestive tract is not sufficiently cleansed in preparation for gastrointestinal surgery, there is risk of infection if, during the surgery, the digestive tract is perforated and food residue inadvertently contaminates the other organs in the individual's body. This is because the digestive tract (particularly the stomach and intestines) is full of a variety of ingested material. As this material makes its way from the stomach toward the anus, the character of the material changes from a watery, green liquid to a nearly solid stool. Further, as the digested food makes its way toward the anus, the amount of bacteria in this liquid material increases. Thus, a goal of removing food residue from the digestive tract is to decrease the amount of bacteria living therein.

With respect to surgery, a substantially or completely residue-free digestive tract can have numerous benefits. If the operation involves the removal of a segment of large intestine, for example, it is technically much easier to reconnect a clean intestine than it is to reconnect an intestine that contains substantial amounts of food residue. Also, a great source of potentially infectious bacteria in the human body is the large intestine. Eliminating these bacteria by removing the food residue from the digestive tract greatly decreases the chance of developing an infection postoperatively. Further, if the surgeon is trying to locate a mass present within the intestine, it is much easier to feel the mass from the outside if the intestine is at least substantially residue free.

Removal of stool matter from the digestive tract is also necessary to effectively screen for gastrointestinal abnormalities, including, but not limited to, cancer such as colon cancer. Since colon cancer is a highly treatable and often curable if detected early, screening tests for detecting premalignant polyps and colorectal cancers at stages early enough for complete removal are very important.

Current colon screening procedures include, for example, barium enema, sigmoidoscopy, fiberoptic endoscopy and virtual endoscopy. The double-contrast barium enema colon screening procedure uses x-ray imaging, which allows a view of the rectum and of the entire colon. Sigmoidoscopy and fiberoptic endoscopy procedures involve snaking a fiberoptic tube through regions of the rectum and colon (part of the large intestine) to view the walls of the intestine.

During either procedure, the physician is able to remove polyps or other abnormalities. Finally, virtual endoscopy utilizes computer reformation of radiologic images to form images of the colon in two or three dimensions. Removing sufficient amounts of stool matter from the colon prior to a colon screening procedure is essential. For some screenings, the colon must be at least substantially free of food residue (e.g., stool matter) in order for the optical or video endoscope or x-ray to accurately image the intestine. Further, stool matter can physically block the progress of the endoscope within the colon, thus preventing the screening. With respect to virtual endoscopy, stool and colon lesions can be indistinguishable in computer tomography or other radiologic modality images. Thus, stool matter can prevent a physician's ability to distinguish pathology from retained fecal debris.

Generally, two procedures are used to remove stool matter from the digestive tract in preparation for surgery or a colon screening. These regimens include: (1) pharmaco-mechanical preparations and (2) antibiotic preparations. Pharmaco-mechanical preparations involve taking drugs that cause the expulsion of the digestive tract's contents in the form of stool and/or diarrhea. An example of such a preparation is a large volume preparation such as Golytely.™, which requires drinking large volumes to physically flush at least some food residue out of the gastrointestinal tract. Another example of such a preparation is a smaller volume preparation such as Fleet.™ Phospho-Soda or magnesium citrate, which are saline-cathartic agents that pull additional fluid from the body to physically flush at least some food residue out of the gastrointestinal tract. Other pharmaco-mechanical preparations include bisacodyl tablets, suppositories or enemas, which work by stimulating peristalsis, i.e., by acting on smooth muscle to cause contractions that physically push food residue out of the gastrointestinal tract.

One problem with some current pharmaco-mechanical preparation techniques is that they dehydrate the patient. Another problem is that some of the preparations can cause a chemical imbalance, and thus may not be safe for use by individuals with kidney disease or a known electrolyte disturbance, for example. Further, mechanical preparation techniques may be difficult to comply with, since they require consuming large volumes of liquid and abstinence from solid foods.

The antibiotic preparation is administered either orally or intravenously. Oral administration requires taking a non-absorbable antibiotic the evening before a medical procedure, such as gastrointestinal surgery. Frequently, however, these antibiotics cause such painful upset stomach or stomach cramps that the preparation is not completed. While intravenous administration of an antibiotic immediately prior to surgery may avoid the painful stomach cramping, many doctors choose not to use the intravenous method. The pharmaco-mechanical preparation and antibiotic preparation are typically used with a clear-liquid diet. Such a diet generally requires the intake of only clear liquids, e.g., clear juices, water and minerals, for a period of about 20- to 36-hours prior to a procedure. A clear liquid diet is used with most stool removal regimens because clear liquids are easily absorbed by the body, reduce stimulation of the digestive system, and leave no solid food residue in the digestive tract. A clear liquid diet may also be used alone to maintain the digestive tract at least substantially free of food residue for a short period of time. Examples of foods that may be consumed on a clear liquid diet are listed in Table 1. Table 2 lists an example of a 24-hour clear liquid diet.

TABLE 1

Examples of Permissible Foods for Clear Liquid Diet Food Groups

| Group | Recommend | Avoid |
| --- | --- | --- |
| Milk & milk products | none | all |
| Vegetables | none | all |
| Fruits | fruit juices without pulp | nectars; all fresh, canned, and frozen fruits |
| Breads & grains | none | all |
| Meat or meat substitutes | none | all |
| Fats & oils | none | all |
| Sweets & desserts | gelatin, fruit ice, Popsicle without pulp, clear hard candy | all others |
| Beverages | coffee; tea; soft drinks; water; lactose-free, low residue supplements if approved by physician | all others |
| Soups | bouillon, consommé fat free broth | all others |

TABLE 2

Example of a 24-Hour Clear Liquid Diet Sample Menu

| Breakfast | Lunch | Dinner |
| --- | --- | --- |
| strained fruit juice 1 cup gelatin 1 cup hot tea with sugar & lemon | consommé ¾ cup strained fruit juice 1 cup fruit ice ½ cup gelatin ½ cup hot tea with sugar & lemon | consommé ¾ cup strained fruit juice 1 cup fruit ice ½ cup gelatin ½ cup hot tea with sugar & lemon |

The diet listed in Table 2 provides about 600 calories, 6 grams (g) of protein and about 209 g of carbohydrates. The diet also provides about 1,500 milligrams (mg) of sodium and 1,440 mg of potassium. The diet contains virtually no fat. Thus, a drawback of the clear liquid diet is that it does not adequately supply sufficient levels of calories and nutrients. Because traditional clear liquid diets provide almost no nutritional value, it is common for individuals to suffer from lightheadedness and drowsiness when adhering to such a diet, thus making it is difficult to perform daily, routine activities. At times, an individual on the clear liquid diet experiences such severe symptoms that a doctor prescribes medication such as metaclopramide, and other anti-nausea drugs. A discussion of clear liquid diets known in the art is contained in Appendix A of U.S. Provisional Application Ser. No. 60/240,569, which is herein incorporated by reference.

It is also known in the art for physicians to recommend a low-fiber, low-residue diet as part of the treatment for certain conditions such as diverticulitis, inflammatory conditions of the bowel, colitis and Chron's disease. A discussion of low fiber, low residue diets known in the art is contained in Appendix B of U.S. Provisional Application Ser. No. 60/240,569, which is herein incorporated by reference. Examples of foods that may be consumed by a patient on a low residue, low fiber diet are listed in Table 3. Table 4 lists an example of a 24-hour low fiber diet.

TABLE 3

Examples of Permissible Foods for Low Fiber Diet
Food Groups

| Group | Recommend | Avoid |
|---|---|---|
| Milk & milk products (2 or more cups daily) | all milk products | Low Residue Diet only 2 cups daily of all milk products |
| Vegetables (3 or more servings daily) | lettuce; vegetable juice without pulp; the following cooked vegetables: yellow squash (without seeds), green beans, wax beans, spinach, pumpkin, eggplant, potatoes, without skin, asparagus, beets, carrots | vegetable juices with pulp, raw vegetables except lettuce, cooked vegetables not on Recommended list |
| Fruits (2 or more servings daily) | fruit juices without pulp, canned fruit except pineapple, ripe bananas, melons | fruit-juices with pulp, canned pineapple, fresh fruit except those on Recommend list, prunes, prune juice, dried fruit, jam, marmalade |
| Starches-Breads & grains (4 or more servings daily) | bread and cereals made from refined flours, pasta, white rice | whole-grain breads, cereals, rice, pasta; bran cereal; oatmeal |
| Meat or meat substitutes (5 or 6 oz daily) | meat, poultry, eggs, seafood | chunky peanut butter, nuts, seeds, dried beans, dried peas |
| Fats & oils (servings depend on caloric needs) | all oils, margarine, butter | coconut |
| Sweets & desserts (servings depend on caloric needs) | all sweets and dessert, except those on the "Avoid" list | desserts containing nuts, coconut |
| Miscellaneous | all, except those on the "Avoid" list | popcorn, pickles, horseradish, relish |

TABLE 4

Example of a 24-Hour Low Fiber Diet
Sample Menu

| Breakfast | Lunch | Dinner |
|---|---|---|
| orange juice ½ cup | fish or veal 3 oz | chicken breast 3 oz |
| cornflakes 1 cup | mashed potatoes ½ cup | medium baked potato without skin |
| poached egg | cooked green beans ½ cup | cooked carrots ½ cup |
| white toast 1 slice | white bread 1 slice | white bread 1 slice |
| margarine 1 tsp | margarine 1 tsp | margarine 1 tsp |
| jelly 1 Tbsp | jelly 1 Tbsp | jelly 1 tbsp |
| skim milk 1 cup | applesauce ½ cup | canned peaches ½ cup |
| coffee ¾ cup | coffee ¾ cup | skim milk ½ cup |
| sugar 1 tsp | sugar 1 tsp | coffee ¾ cup |
| non-dairy creamer | non-dairy creamer | sugar 1 tsp |
| salt/pepper | salt/pepper | non-dairy creamer |
| | | salt/pepper |

The diet listed above in Table 4 provides approximately 1,576 calories, 89 g of protein and 215 g of carbohydrates. The diet also provides 45 g of fat, about 2,817 mg of sodium and 3,510 mg of potassium. It also provides approximately 15 g of dietary fiber.

There is, therefore, a need for a nutritional diet which, when coordinated with a laxative regimen, effectively removes food residue from the digestive tract while providing the user with a sufficient level of calories and nutrition to conduct routine, daily activities. In addition, there is a need for a dietary regimen to be used in conjunction with a laxative regimen, while at the same time facilitating user compliance to the diet, since current cleansing techniques are often difficult or painful to complete, or require a high-degree of will power. The consequences of noncompliance can be great. For example, noncompliance can result in an ineffective colon screening or a post operative infection.

Additionally, there is a need for a nutritional dietary regimen which is readily useable and convenient, while also ensuring that the diet is exactly followed by the user. This is especially important for sick or incapacitated individuals incapable of acquiring or preparing specific food items.

SUMMARY OF THE INVENTION

It is an object of the present invention to provide a nutritional dietary system, formulation, kit and method for use in preparing an individual for a predetermined activity which requires a clean digestive tract, particularly the colon.

Additionally, it is an object of the present invention to provide a nutritional dietary system, formulation, kit and method to be used with a laxative regimen for preparing individuals for predetermined surgery including, but not limited to, gastrointestinal surgery.

It is also an object of the present invention to provide a nutritional dietary system, formulation, kit and method to be used with a laxative regimen for preparing individuals for predetermined medical diagnostic procedure including, but not limited to, colon screening.

Further, it is an object of the present invention to provide a variety of individually prepackaged, ready to eat or easy to prepare solid or liquid foods which can be consumed as part of a regimen for removing at least some food residue from the digestive tract.

It is another object of the present invention to provide a nutritional dietary regimen comprising low amounts of fat, dietary fiber and sufficient solid matter, as well as sufficient calories and nutrition such that routine, daily activities may be performed and no nutritional detriment is suffered by the user while utilizing the present invention.

Further, it is another object of the present invention that the dietary regimen provide a variety of prepackaged ready to eat or easy to prepare liquid or solid foods which are readily obtainable from a kit and which may be stored on a shelf without loss of nutritional benefits. An advantage of such a kit is that food preparation is simple and convenient, thus resulting in higher user satisfaction and compliance.

It is also an object of the present invention to provide easy to follow directions for carrying out the nutritional dietary regimen of the present invention.

Additionally, it is an object of the present invention to provide a kit containing individually prepackaged ready-to-eat or easy-to-prepare liquid or solid food items for consumption at various times throughout approximately a 24-hour period.

Other objects, features, and advantages of the present invention will be apparent to those of ordinary skill in the art in view of the following detailed description of the invention and drawings.

BRIEF DESCRIPTION OF THE DRAWINGS

FIG. 1 is a non-limiting example of a unifying container comprising the food items of the present invention.

FIG. 2 is a non-limiting example of a device for recording the consumption of the food items utilized in the present invention.

FIGS. 6a-6c are non-limiting examples of customized kits comprising the food items of the present invention.

FIG. 7 represents a non-limiting example of customizing a kit comprising the food items of the present invention.

FIG. 10 is a non-limiting diagram of an alternative embodiment of the present invention.

FIG. 11 is a non-limiting example of instructions for utilization in the present invention.

FIGS. 12 and 13 are non-limiting examples of a dietary regimen of the present invention.

FIGS. 14 and 15 are non-limiting examples of a low residue nutritional protocol for utilization in the present invention.

FIGS. 16-19 are non-limiting examples of instructions for utilization in the present invention.

DETAILED DESCRIPTION OF THE INVENTION

Figure 3:
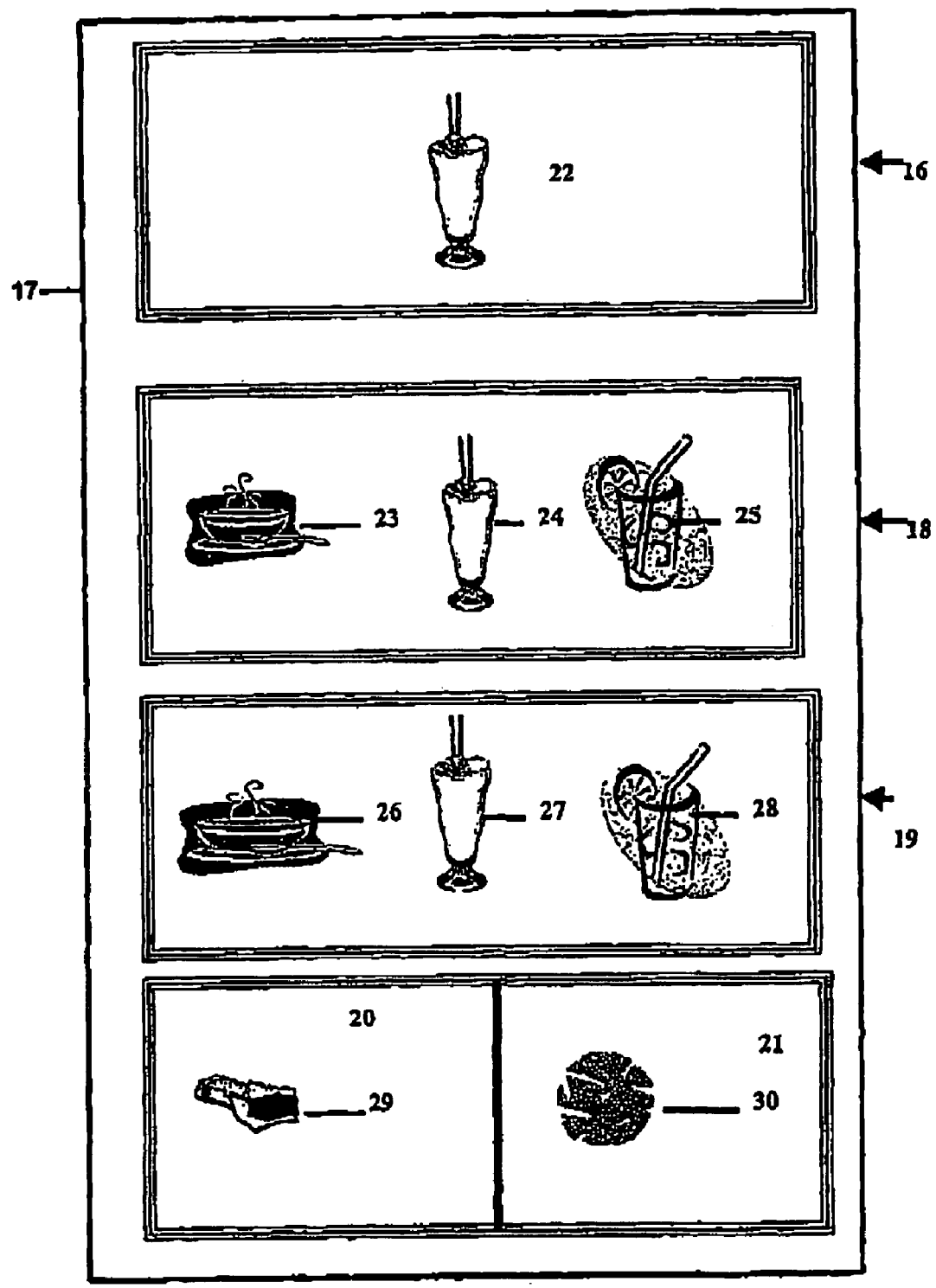
FIG. 3 is a non-limiting example of a kit comprising of food items of the present invention.

The present invention provides a nutritional dietary system, kit, formulation and method for use in preparing an individual for a predetermined activity, including but not limited to, an activity which requires a clean digestive tract, particularly the colon. As used herein, the term "clean digestive tract" includes, but is not limited to, a digestive tract that has reduced or low amounts of food residue or requires removal of at least some food residue such that the residue does not impede or otherwise adversely affect the predetermined activity or the outcome of such activity. A predetermined activity includes, but is not limited to, any activity which requires a clean digestive tract. In one embodiment, the predetermined activity may include, but is not limited to, a medical activity such as a surgery or a diagnostic procedure. For example, a surgery that may require low amounts of residue or require at least some removal of residue from the digestive tract includes, but is not limited to, surgery on the esophagus, stomach, duodenum, liver, pancreas, intestines, rectum, anus or any other type of gastrointestinal surgery. A diagnostic procedure that may require low amounts of residue or require at least some removal of residue from the digestive tract includes, but is not limited to, gastrointestinal screening (i.e., colon screening) such as fiberoptic endoscopy, sigmoidoscopy, virtual endoscopy, pilloscopy (scope in a pill) and double-contrast barium enema. In some cases, the above procedures require a substantially residue-free digestive tract in order for such procedures to be performed properly. It may also be necessary to keep the digestive tract essentially stool-free on a short-term basis pre- or post-operatively to prevent infection and promote healing.

Specifically, the dietary regimen of the present invention comprises one or more food items. These items include any liquid, solid or semi-solid food providing, in whole or in part, the requisite amounts of fat, dietary fiber and solid matter described herein. Such food items may include, but are not limited to, soup products, protein supplements, grain foods, starch foods, fruit or vegetable foods, nutritional drinks or beverages.

In use, the food items of the present invention are preferably consumed over about a 20- to 36 hour period, or a 20- to 24-hour period, or a 24- to 28-hour period, more preferably over about a 24-hour period prior to a predetermined activity. In addition, such food items may be consumed over a 72-hour period, a 48-hour period, a 24- to 36-hour period, a 36- to 48-hour period and 48- to 72-hour period prior to a predetermined activity.

Additionally, the present invention supplies sufficient calories and nutrition such that adverse effects such as lightheadedness, drowsiness, irritability, hunger and headaches, which are traditionally associated with the prior art diets, are minimized while utilizing the present invention. Thus, in one embodiment, daily activities can be performed while using the present invention. Further, in another embodiment, the food components are ready to eat or easy to prepare and good-tasting, thereby facilitating user satisfaction and compliance with the present invention.

A. Nutrition

1. Calories

The food items of the present invention may collectively provide an individual an appropriate caloric intake level over the time period in which the invention is utilized. In one alternative embodiment, based on about a 20- to about a 36-hour dietary regimen, the food items may collectively provide at least 100 calories, preferably in a range of about 400 to about 3,000 calories, and more preferably in a range of about 600 to about 2,000 calories. In an alternative embodiment, based on about a 20- to 36-hour dietary regimen, the food items may collectively provide more than about 600 calories, more preferably in a range of about 1,000 to about 1,800 calories, more preferably in a range of about 1,500 to about 1,600 calories, and most preferably from about 1,500 calories. In another alternative embodiment, the food items may collectively provide a range of about 1,000 to about 2,000 calories, from about 1,400 to about 1,600 calories, and from about 1,600 calories. In another alternative embodiment, the food items may collectively provide 1,000 or more calories. The total calories of the food items of the present invention are preferably sufficient to enable an average sized individual to perform routine daily activities without experiencing the dizziness, fatigue and lightheadedness ordinarily experienced with a clear liquid diet. Thus, the dietary system of the present invention is an improvement over traditional clear liquid diets because, typically, the clear liquid diet does not provide adequate calories, and often results in feelings of lightheadedness and drowsiness.

In another alternative embodiment of the present invention, based on about a 20 to about a 36-hour dietary regimen, the food items may collectively provide more than about 0.5 g, or about 0.75 g, 1 g, 1.5 g, 2 g, 3 g, 4 g, 5 g, 6 g, 7 g, 8 g, 9 g, 10 g, 11 g, 12 g, 13 g, 14 g, 15 g, of dietary fiber.

2. Dietary Fiber

The food items of the present invention may collectively provide an individual an appropriate amount of dietary fiber over the time period in which the invention is utilized. In one alternative embodiment, based on about a 20- to 36-hour dietary regimen, the food items may collectively provide at least 0.5 g of dietary fiber, preferably in a range of about 0.5 g to about 20 g of dietary fiber, more preferably in a range of about 0.5 g to about 10 g, even more preferably in a range of about 2 g to about 8 g, even more preferably from about 2 g to about 6 grams, and most preferably about 5 g.

In an alternative embodiment, based on about a 20-to about a 36-hour dietary regimen, the food items may collectively provide less than about 15 g of dietary fiber. Also, in an alternative embodiment, based on about a 20-to about a 36-hour dietary regimen, the food items may collectively provide about 20 g to about 60 g of dietary fiber, or 20 g to 30 g, 30 g to 40 g, 40 g to 50 g, 50 g to 60 g, or 60 g to 100 g. It has been found that a dietary regimen containing low amounts of dietary fiber, when used in conjunction with a laxative, may eliminate the need for consuming high-volume purgative drinks or high sodium cathartic cleansing drinks, which can be difficult to consume for some individuals.

In another alternative embodiment, the amount of dietary fiber utilized in the present invention may help to promote sufficient peristalsis to cause at least some of the food to be moved through the digestive tract, thus facilitating preparation of the digestive tract prior to the predetermined activity.

Providing an individual the amounts of fiber described herein (including, but not limited to 2 g to 8 g) provided unexpected results, in that sufficient and/or increased amounts of fiber can be consumed without impeding the cleansing process of the digestive tract. It was believed that providing high amounts of fiber would form too much food residue in the digestive tract; but low amounts of fiber would not promote and/or facilitate the cleansing process, for example, through peristalsis. In the present invention, the amounts of fiber are sufficiently low enough so as not to generate excessive amounts of food residue, yet high enough to promote and/or facilitate the cleansing of the digestive tract.

3. Protein

The food items of the present invention may collectively provide an appropriate amount of protein over the time period in which the invention is utilized by an individual. Preferably, the proteins are derived from any plant source (e.g., rice, soy), as well as animal sources, including but not limited to meats, poultry and fish or veal. In one alternative embodiment, based on about a 20- to 36-hour dietary regimen, the food items of the present invention may collectively provide at least 1 g of protein, preferably in a range of about 1 g to about 70 g, more preferably in a range of about 20 g to about 60 g, and most preferably in a range of about 30 g to about 50 g.

The dietary regimen of the present invention may also include about 3 to 7 ounces (oz), preferably about 3 oz, of chicken, fish, veal or any other meat or meat by-product containing the amounts of dietary fiber and fat described as part of the present invention.

4. Carbohydrates

The food items of the present invention may collectively provide an individual sufficient carbohydrates over the time period in which the dietary regimen of the present invention is utilized. In one alternative embodiment, based on about a 20- to 36-hour dietary regimen, the food items of the present invention may collectively provide at least 1 g of carbohydrates, preferably in a range of about 2 g to about 500 g, more preferably in a range of about 100 g to about 400 g, even more preferably in a range of about 200 g to about 300 g, and most preferably in a range of about 220 g to 260 g. In another alternative embodiment, the food items of the present invention may collectively provide at least 100 g of carbohydrates.

5. Fats

Generally, fat delays the emptying process of the stomach. The more fat in a particular food, the longer it takes for the stomach to digest that food. The food items of the present invention may collectively provide an individual amount of fat over the time period in which the dietary regimen of the present invention is utilized. In one alternative embodiment, based on about a 20- to 36-hour dietary regimen, the food items of the present invention may collectively provide less than approximately 30% of the calories derived from fat, preferably in a range of about 5% to about 30%, and most preferably a range of about 10% to about 20%.

In an alternative embodiment, based on about a 20-to 36-hour dietary regimen, the food items of the present invention collectively provide at least 0.5% of the calories derived from fat. Further, in another embodiment, based on about a 20-to about a 36-hour dietary regimen, the food items of the present invention provide less than approximately 25% calories derived from fat, and more preferably from about 0.5% to about 20%. In another alternative embodiment, the food items of the present invention may collectively provide about 30% to about 50% of calories derived from fat, or 50% to 60%.

6. Sodium and Potassium

Based on about a 20- to 36-hour dietary regimen, the food items of the present invention may collectively provide sodium in the range of about 100 mg to about 3000 mg, preferably in an amount less than about 2400 mg. In the present invention, the sodium content may be adjusted by utilizing other elements or "non-salt" compositions in the food items. Such "non-salt" compositions include, for example, potassium salts such as potassium chloride (KCl) or potassium lactate. The present invention may also contain potassium in an amount less than 1500 mg, and more preferably in an amount less than 1000 mg.

7. Sugars

Based on about a 20- to 36-hour dietary regimen, the food items of the present invention may collectively provide sugars in a range of about 0.5 g to about 500 g, preferably in a range of about 50 g to about 200 g, and more preferably in a range of about 100 g to about 200 g.

8. Vitamins and Minerals

In an alternative embodiment, the individual food items of the present invention may collectively provide vitamins and minerals in a range of at least 10% to about 100% USRDA over about a 20- to 36-hour period prior to a predetermined activity. Such vitamins and minerals, may include, for example, vitamins A, B.sub.1, B.sub.2, B.sub.3, B.sub.6, B.sub.12, C, D, E, and K, Biotin, Calcium, Copper, Chromium Folic Acid, Iodine, Iron, Magnesium, Manganese, Niacin, Pantothenic Acid, Phosphorus, Riboflavin, Thiamin and Zinc. Also, each of the individual food items may contain or be fortified in such a way as to provide at least approximately 25% USRDA, and up to 100% USRDA of vitamins and minerals.

The amount of nutrition in the food items of the present invention represents an improvement over traditional dietary regimens used as part of a regimen for removing residue from the digestive tract. For instance, a disadvantage of the clear liquid diet is that it does not provide adequate nutrition, and thus may cause symptoms such as dizziness and fatigue. As a result, it is often difficult for individuals undergoing the clear liquid diet to conduct daily activities or to adhere to the dietary regimen. Conversely, the food items of the present invention provide sufficient levels of nutrition, while still facilitating the removal of sufficient residue from the digestive tract.

9. Solid-Material

The individual food items of the present invention may individually or collectively provide a suitable amount of solid material, which includes particulate material. In one alternative embodiment, based on about a 20-to about a 36-hour dietary regimen, the present invention may provide up to approximately 1000 grams of solid material, as measured in dry form. In another embodiment, the present invention provides about 10 g to about 1000 grams of solid material, preferably about 100 g to about 800 g, more preferably about 100 g to about 900 g, more preferably about 200 g to about 700 g, and most preferably about 400 g to about 600 g. Table 5 shows the approximate total weight of one preferred alternative embodiment of the dietary regimen of the present invention:

TABLE 5

Example of Approximate Dry Weight of Dietary Regimen

| Food Item | Approximate Weight Dry (g) | Approximate Net Weight Prepared (g) |
|---|---|---|
| Stroganoff | 37.62 | 163.11 |
| Chicken Noodle Soup | 36.39 | 160.88 |
| Potato Poppers | 29.36 | 29.36 |
| Applesauce | 70.15 | 113.40 |
| Vanilla Shake (3) | 66.96 (3) | 261.46 (3) |
| Lemon Drink Mix (2) | 6.95 (2) | 216.13 (2) |
| Chocolate Power Bar (2) | 50.69 (2) | 50.69 (2) |
| Total | 489.68 | 1784.77 |
| Total Percentage of Solid Material Included in Diet | 27.4 | — |

In another alternative embodiment of the present invention, based on about a 20-to about a 36-hour dietary regimen, the food items may collectively comprise at least about 1% by weight of solid material, preferably in a range of about 1% to about 70%, more preferably about 10% to about 30%, and most preferably about 20% to about 30%. In another embodiment, the food items of the present invention may collectively provide about 30% to 40%, 40% to 50%, 50% to 60%, 60% to 70%, 70% to 80%, 80% to 90%, and 90% to 100% by weight of solid material. In another embodiment, the food items of the present invention, individually or collectively, provide sufficient solid material to cause natural peristalsis in the digestive tract when consumed.

In another alternative embodiment, the solid material content of the present invention may promote sufficient peristalsis to cause at least some of the food to be moved through the digestive tract, thus facilitating the preparation of the digestive tract prior to the predetermined activity.

B. Food Items of the Present Invention

The present invention comprises one or more food items. Each food item of the present invention may be individually prepackaged. In addition, one or more of the food items may be nutritionally enhanced by fortification of vitamins and minerals.

The individual food items may be prepared by processing, e.g., mixing, precooking, cooking, freezing, dehydrating or freeze-drying, such that the meal may be maintained in a frozen or dry condition for an extended period. Additionally, an individual food item may be packaged in such a way that, before consumption, the food item must by mixed by hand or blender, cooked by placing the food component on a stove top, in an oven or microwave, or prepared by adding cool, hot or boiling water or by submerging the food item into boiling water. One or more of the food items of the present invention may be shelf-stable. Preferably, a food item has a sufficiently long storage or shelf-life such that the present invention may be stored in advance of consumption. A storage or shelf-life under retail conditions in a range of about six to twelve months is desirable.

An individual food item suitable for use in the present invention is one that forms no food residue in the digestive tract or that forms an amount of food residue which does not impede or otherwise adversely affect a predetermined activity. Such predetermined activities include, but are not limited to, any activity which requires a clean digestive tract including, but not limited to, a medical activity such as gastrointestinal surgery or a diagnostic procedure, e.g., colon screening. Preferably, the food items of the dietary regimen of the present invention collectively comprises low amounts of fat, dietary fiber, and contain about at least 1% by weight of solid material.

Individual food items of the present invention may be in the form of solids, semi-solids or liquids and may include, but are not limited to, soup products, protein supplements, grain foods, starch foods, fruit or vegetables foods, nutritional drinks and beverages. In contrast to the prior art, the liquid food items of the present invention need not be clear. Each of the food items of the present invention are discussed in more detail below.

The coloring used in the food items of the present invention, particularly in the nutritional drinks and beverages, may be limited by the purpose for which the food residue is being removed from the individual's digestive tract. For instance, a food item containing red coloring may not be suitable for an individual preparing for an optical colonoscopy, as the red coloring may interfere with the test results of such procedure.

1. Soup Products

Soup products suitable for use in the present invention include any soup product that forms no food residue in the digestive tract or that forms an amount of residue which does not impede or adversely affect a predetermined activity or the outcome of such activity. Such soup products include, but are not limited to any clear soup without milk or cream, flavored bouillon/broth, strained soup, vegetable soup, soup containing beef, pork, poultry, fish or veal, soup with legumes, soup with pasta, soup with rice, chicken noodle soup, chicken and rice soup and the like.

A soup product suitable for use in the present invention includes, but is not limited to, a chicken flavored broth comprising salt, corn syrup solids, sugar, hydrolyzed corn and soy proteins, monosodium glutamate, chicken, autolyzed yeast extract, onion powder, garlic powder, silicon dioxide, turmeric, parsley, natural flavor, maltodextrin, chicken fat, partially hydrogenated soybean and/or cottonseed oils, spices, disodium inosinate, disodium guanylate, hydrolyzed wheat gluten, BHA, citric acid, thiamine hydrochloride.

Another soup product suitable for use in the present invention includes, but is not limited to, a chicken flavored noodle soup comprising enriched pasta product (made from enriched durum flour (niacin, iron (ferrous sulfate), thiamine mononitrate, riboflavin), textured vegetable protein, soup base (dextrose, corn starch, salt, vegetable oil (soybean)), vegetable shortening, hydrolyzed vegetable protein, spices, diced carrots, tumeric.

Another soup product suitable for use in the present invention includes, but is not limited to, a naturally and artificially flavored chicken noodle soup comprising noodles (durum flour, niacin, ferrous fumarate, thiamine mononitrate, riboflavin, folic acid), partially hydrogenated vegetable oil (canola, soybean, cottonseed), dextrose, potato starch, natural and artificial flavor, corn syrup solids, salt, whey, peas, carrots, onion powder, hydrolyzed vegetable protein (corn, soy), garlic powder, sodium caseinate, sugar spice and color, disodium inosinate, disodium guanylate, mono- and diglycerides, dipotassium phosphate, soy four, cornstarch, chicken fat, maltodextrin, soy lecithin, alpha tocopherol acetate, ascorbic acid, ferrous fumarate, chicken, niacinamide, zinc oxide, manganese sulfate, caldium pantothenate, vitamin A palmitate, phytonadione, copper sulfate, pyrdoxine hydrochloride, riboflavin, thiamine hydrochloride, vitamin B12, vitamin D3, folic acid, sodium molybdate, chromium chloride, biotin, potassium iodide, sodium selenite.

In one alternative embodiment of the present invention, an appropriate serving of a suitable chicken soup (naturally and artificially flavored) may comprise the characteristics listed in Table 6. Additionally, the soup may contain vitamins and/or minerals such that it provides the level of nutrition listed in Table 7.

TABLE 6

Chicken Noodle Soup, Naturally and Artificially Flavored

Serving Size: 1 Container. (27 g)
Servings Per Container: 1
Amount Per Serving
Calories 100  Calories from Fat

| | % Daily Value* |
|---|---|
| Total Fat 2.5 g | 4% |
| Saturated Fat 0.5 g | 3% |
| Cholesterol 0 mg | 0% |
| Sodium 650 mg | 27% |
| Potassium 150 mg | 4% |
| Total Carbohydrate 18 g | 6% |
| Dietary Fiber less than 1 g | 3% |
| Sugars 5 g | |
| Protein 2 g | |

*Percent daily value based on a 2,000 calorie diet.

TABLE 7

Vitamins and Minerals

| | % Daily Value* |
|---|---|
| Vitamin A | 35% |
| Calcium | 2% |
| Vitamin D | 20% |
| Vitamin K | 15% |
| Riboflavin | 30% |
| Vitamin B6 | 25% |
| Vitamin B12 | 25% |
| Pantothenic Acid | 25% |
| Zinc | 20% |
| Copper | 25% |
| Chromium | 10% |
| Vitamin C | 25% |
| Iron | 25% |
| Vitamin E | 20% |
| Thiamin | 35% |
| Niacin | 25% |
| Folate | 30% |
| Biotin | 20% |
| Iodine | 20% |
| Selenium | 20% |
| Manganese | 40% |
| Molybdenum | 40% |

*Percent daily value based on a 2,000 calorie diet.

2. Protein Supplements

Protein supplements suitable for use in the present invention include any protein supplement that forms no food residue in the digestive tract or that forms an amount of residue which does not impede or adversely affect a predetermined activity or the outcome of such activity Such protein supplements may take a variety of forms, including, but not limited to, protein bars, energy bars, nutrition bars, sports bars and baked good such as cookies and cakes.

A protein supplement suitable for use in the present invention includes, but is not limited to, a chocolate protein bar comprising soy protein isolate, maltitol syrup, calcium caseinate, honey, glycerine, sugar, palm kernel oil, cocoa powder, milk protein concentrate, whey protein isolate, rice flour, lecithin, and less than two percent of less of natural flavors, chicory extract, water canola oil, sunflower seed oil, malt, salt, whey, tumeric oleoresin color, annatto extract color and possibly traces of various nuts and seeds.

Another protein supplement suitable for use in the present invention includes, but is not limited to, a lemon crunch protein bar comprising soy protein isolate, maltitol syrup, calcium caseinate, high fructose corn syrup, whey protein isolate, hydrogenated palm kernel oil, sugar, glycerine, honey, hydrolyzed gelatin, lecithin; and less than two percent of less of canola oil, rice flour, corn syrup, water, sunflower seed oil, chicory extract, whey, natural and artificial flavors, malic acid, yogurt solids, citric acid, salt, tumeric oleoresin color, malt, artificial color, annatto extract color and possibly traces of various nuts and seeds.

Another protein supplement suitable for use in the present invention includes, but is not limited to, a chocolate protein bar comprising high maltose corn syrup, high fructose corn syrup, calcium caseinate, soy protein isolate, cocoa (processed with alkali), sugar, fractionated palm kernel oil, toasted soy pieces, cocoa butter, nonfat milk, natural flavor, glycerine, lactose, calcium phosphate, soy lecitin, dextrose, magnesium oxide, salt, ascorbic acid, maltodextrin, ferric orthophosphate, alpha tocopherol acetate, niacinamide, zinc oxide, copper gluconate, calcium panthothenate, pyridoxine hydrochloride, riboflavin, thiamine mononitrate, vitamin A palmitate, folic acid, biotin, potassium iodide, vitamin D3, vitamin B12.

In one alternative embodiment of the present invention, an appropriate serving of a chocolate flavored protein bar may comprise the characteristics listed in Table 8. Additionally, the chocolate protein bar may contain vitamins and/or minerals such that it provides the level of nutrition listed in Table 9.

TABLE 8

Chocolate Flavored Protein Bar

Serving Size: 1 Container. (45 g)
Servings Per Container: 1 Bar
Amount Per Serving

| Calories 170 | Calories from Fat |
|---|---|
|  | % Daily Value* |
| Total Fat 5 g | 8% |
| Saturated Fat 30.5 g | 18% |
| Cholesterol 0 mg | 0% |
| Sodium 125 mg | 5% |
| Potassium 190 mg | 5% |
| Total Carbohydrate 24 g | 8% |
| Dietary Fiber 1 g | 4% |
| Sugars 15 g |  |
| Protein 10 g |  |

*Percent daily value based on a 2,000 calorie diet.

TABLE 9

Vitamins and Minerals

|  | % Daily Value |
|---|---|
| Vitamin A | 20% |
| Calcium | 15% |
| Vitamin D | 20% |
| Thiamin | 20% |
| Niacin | 20% |
| Folate | 20% |
| Biotin | 20% |
| Phosphorus | 15% |
| Magnesium | 20% |
| Copper | 20% |
| Vitamin C | 20% |
| Iron | 30% |
| Vitamin E | 20% |
| Riboflavin | 20% |
| Vitamin B6 | 20% |
| Vitamin B12 | 20% |
| Pantothenic Acid | 20% |
| Iodine | 20% |
| Zinc | 20% |

* Percent daily value based on a 2,000 calorie diet.

3. Grain Foods

Grain foods suitable for use in the present invention include any grain-enriched food that forms no food residue in the digestive tract or that forms an amount of residue which does not impede or adversely affect a predetermined activity or the outcome of such activity. Such grain foods may include, for example, pasta, rice, soy, package of potato poppers, cereal, cereal bars, bread and the like. Such grain foods may be used in combination with other complimentary foods to enhance palatability including, but not limited to, sauces, vegetables, fruit, herbs, spices, seasonings, butter and artificial flavorings.

A grain food suitable for use in the present invention includes, but is not limited to, a caramel mini package of potato poppers comprising rice (preferably white rice), corn (with germ removed), evaporated cane juice, natural flavor, salt and caramel color.

Another grain food suitable for use in the present invention includes, but is not limited to, pasta with stroganoff flavored sauce comprising pasta (semolina), modified food starch, non-fat mild, cream, natural flavor, autolyzed yeast extracts, cultured sour cream, mushrooms, onion powder, salt, tomato powder, garlic powder, dextrose, non-fat dry milk, whey, whey protein concentrate, partially hydrogenated canola oil, xanthan gum, guar gum, corn syrup solids, parsley, soy sauce (wheat and soybean, salt), caramel added for color, paprika added for color, maltodextrin, spice, soy lecithin, yeast extract, sodium caseinate, mixed tocopherols added to protect flavor, ascorbol palmitate added to protect flavor, alpha tocopherol acetate, ascorbic acid, mono-and diglycerides, ferrous fumarate, dipotassium phosphate, silicon dioxide, niacinamide, zinc oxide, manganese sulfate, calcium pantothenate, vitamin A palmitate, phytonadione, copper sulfate, pyridoxine hydrochloride, riboflavin, thiamine hydrochloride, vitamin B12, vitamin D3, folic acid, sodium molydate, chromium chloride, biotin, potassium iodide and sodium selenite.

In one alternative embodiment of the present invention, an appropriate serving of pasta with stroganoff flavored sauce may comprise the characteristics listed in Table 10. Additionally, the pasta with stroganoff flavored sauce may contain vitamins and/or minerals such that it provides the level of nutrition listed in Table 11.

TABLE 10

Pasta with Stroganoff Flavored Sauce
Nutrition Facts

Serving Size: 1 Container. (37 g)
Servings Per Container: 1
Amount Per Serving

| Calories 140 | Calories from Fat 30 |
|---|---|
|  | % Daily Value* |
| Total Fat 3 g | 5% |
| Saturated Fat 2 g | 10% |
| Cholesterol 10 mg | 3% |
| Sodium 490 mg | 20% |
| Potassium 160 mg | 5% |
| Total Carbohydrate 24 g | 8% |
| Dietary Fiber less than 1 g | 3% |
| Sugars 4 g |  |
| Protein 5 g |  |

*Percent daily value based on a 2,000 calorie diet.

TABLE 11

Vitamins and Minerals

|  | % Daily Value |
|---|---|
| Vitamin A | 25% |
| Calcium | 6% |
| Vitamin D | 20% |
| Vitamin K | 15% |
| Riboflavin | 30% |
| Vitamin B6 | 25% |
| Vitamin B12 | 25% |
| Pantothenic Acid | 25% |
| Zinc | 20% |
| Copper | 25% |
| Chromium | 10% |
| Vitamin C | 25% |
| Iron | 25% |
| Vitamin E | 20% |

TABLE 11-continued

| Vitamins and Minerals | |
|---|---|
| | % Daily Value |
| Thiamin | 25% |
| Niacin | 25% |
| Folate | 20% |
| Biotin | 20% |
| Iodine | 20% |
| Selenium | 20% |
| Manganese | 40% |
| Molybdenum | 40% |

* Percent daily value based on a 2,000 calorie diet.

4. Starch Foods

Starch foods suitable for use in the present invention include any starch-enriched food that forms no residue in the digestive tract or that forms an amount of residue which does not impede or adversely affect a predetermined activity or the outcome of such activity for which at least some removal of food residue from the digestive tract is sought.

A starch food suitable for use in the present invention includes, but is not limited to, foods comprising potato, package of potato poppers, pasta, boiled rice, potato popper, finely-milled wheat or cornbread, soda cracker, tapioca pudding, refined cooked cereal, yam, light white rye without seeds, roll without seeds, biscuit, pancake, sweet potato without skin or grits.

In one alternative embodiment of the present invention, an appropriate serving of potato poppers may comprise the characteristics listed in Table 12. Additionally, the potato poppers may contain vitamins and/or minerals such that it provides the level of nutrition listed in Table 13.

TABLE 12

Potato Poppers
Nutrition Facts

Serving Size: about 50 pieces. (28 g)
Servings Per Container: 1
Amount Per Serving

| Calories 98 | Calories from Fat 10 |
|---|---|
| | % Daily Value* |
| Total Fat 1 g | 2% |
| Saturated Fat 0 g | 0% |
| Cholesterol 0 mg | 0% |
| Sodium 168 mg | 5% |
| Total Carbohydrate 10 g | 3% |
| Dietary Fiber 0 g | 0% |
| Sugars 0 g | |
| Protein 1 g | |

*Percent daily value based on a 2,000 calorie diet.

TABLE 13

| Vitamins and Minerals | |
|---|---|
| | % Daily Value |
| Vitamin A | 0% |
| Calcium | 0% |
| Vitamin C | 6% |
| Iron | 6% |

* Percent daily value based on a 2,000 calorie diet.

5. Fruit or Vegetable Foods

Fruit or vegetable foods suitable for use in the present invention include any fruit- or vegetable-based food that forms no food residue in the digestive tract or forms an amount of residue which does not impede or adversely affect an intended activity or the outcome of such activity. Such fruit- or vegetable-based foods include, but are not limited to, fruit ice, fruit puree, pears, bananas, fruit juices without pulp and canned fruits.

A fruit-based food suitable for use in the present invention includes, but is not limited to, a cinnamon flavored pears, bananas or apple sauce comprising apples, corn syrup, high-fructose corn syrup, sugar, water, cinnamon, natural flavor, ascorbic acid (vitamin C).

In one alternative embodiment of the present invention, an appropriate serving of cinnamon flavored pears, bananas or apple sauce may comprise the characteristics listed in Table 14. Additionally, the cinnamon flavored pears, bananas or apple sauce may contain vitamins and/or minerals such that it provides the level of nutrition listed in Table 15.

TABLE 14

Cinnamon Pears, bananas or apple sauce
Nutrition Facts

Serving Size: 113 g (4 oz)
Servings Per Container: 1
Amount Per Serving

| Calories 100 | Calories from Fat 0 |
|---|---|
| | % Daily Value* |
| Total Fat 0 g | 0% |
| Sodium 15 mg | 1% |
| Total Carbohydrate 23 g | 8% |
| Dietary Fiber 1 g | 4% |
| Sugars 21 g | |
| Protein 0 g | |

*Percent daily value based on a 2,000 calorie diet.

TABLE 15

| Vitamins and Minerals | |
|---|---|
| | % Daily Value |
| Vitamin C | 100% |
| Calcium | 0% |
| Vitamin A | 0% |
| Iron | 0% |

* Percent daily value based on a 2,000 calorie diet.

6. Nutritional Drinks

Nutritional drinks suitable for use in the present invention include any nutritional drink that forms no foods residue in the digestive tract or that forms an amount of residue which does not impede or adversely affect an intended activity or the outcome of such activity. Such nutritional drinks may include, but are not limited to, a blend of natural and/or artificial ingredients formed into a nutrient enriched drink. Further, nutritional drinks of the present invention may be compounded in dry form into a nutritional powder mixture which is readily soluble in a fluid such as water. Such nutritional drinks may include various compounds including water, dextrose, glycine, electrolytes (including sodium potassium and chloride), sodium carbonate and other vitamin and mineral supplements, and may be flavored with artificial and natural flavors. Flavors of the nutritional drinks may include, but are not limited to, chocolate, vanilla and coffee. When digested, the nutritional drink may provide the patient with a pre-determined level of nutrition and a sense of well-being.

A nutritional drink suitable for use in the present invention includes, but is not limited to, a vanilla flavored shake comprising fructose, calcium caseinate, maltodextrin, emulsified soy bean oil, natural and artificial vanilla flavor, xanthan gum, calcium phosphate, magnesium oxide, beta carotene, ascorbic acid (vitamin c), di-alpha tocopheryl acetate, ferrous sulfate, oxide, niacinamide, d-calcium pantothenate, vitamin a palmitate, copper sulfate, manganese sulfate, pyridoxine hydrochloride, riboflavin, thiamine hydrochloride (vitamin b-1), folic acid, biotin, vitamin d-3, potassium iodide and cyanocobalamin.

Another nutritional drink suitable for use in the present invention includes, but is not limited to, a vanilla flavored nutritional shake comprising fructose, soy protein, rice polishing powder, soy EFA powder, vanilla flavor, di-calcium phosphate anhydrous, guar gum, magnesium oxide, vitamin C, ferrous fumarate, biotin, vitamin E succinate, niacinamide, vitamin A palmitate, zinc oxide, copper gluconate, calcium pantothenate, manganese sulfate, pyridoxine hydrochloride, thiamine hydrochloride, riboflavin, vitamin D, cyanacobalamin, folic acid and potassium iodide.

In one alternative embodiment of the present invention, an appropriate serving of a vanilla nutritional shake may comprise the characteristics listed in Table 16. Additionally, the vanilla nutritional shake may contain vitamins and/or minerals such that it provides the level of nutrition listed in Table 17.

TABLE 16

Vanilla Nutritional Shake
Nutrition Facts

Serving Size: 1 Packet. (58 g)
Servings Per Container: 1
Amount Per Serving

| Calories 240 | Calories from Fat 35 |
|---|---|
| | % Daily Value* |
| Total Fat 4 g | 6% |
| Cholesterol 0 mg | 0% |
| Sodium 150 mg | 6% |
| Potassium 100 mg | 3% |
| Total Carbohydrate 41 g | 14% |
| Dietary Fiber 0 g | 0% |
| Sugars 26 g | |
| Protein 9 g | 18% |

*Percent daily value based on a 2,000 calorie diet.

TABLE 17

Vitamins and Minerals

| | % Daily Value |
|---|---|
| Vitamin A 1250 IU | 25% |
| Calcium 250 mg | 25% |
| Vitamin D 100 IU | 25% |
| Thiamin 375 mcg | 25% |
| Niacin 5 mg | 25% |
| Folate 100 mcg | 25% |
| Biotin 75 mcg | 25% |
| Phosphorus 250 mg | 25% |
| Magnesium 100 mg | 25% |
| Copper 500 mcg | 25% |
| Vitamin C 30 mg | 50% |
| Iron 4.5 mg | 25% |
| Vitamin E 7.5 IU | 25% |
| Riboflavin 425 mcg | 25% |
| Vitamin B6 500 mcg | 25% |
| Vitamin B12 1.5 mcg | 25% |
| Pantothenic Acid 2.5 mg | 25% |

TABLE 17-continued

Vitamins and Minerals

| | % Daily Value |
|---|---|
| Iodine 37.5 mg | 25% |
| Zinc 3.75 mg | 25% |
| Manganese 500 mcg | 25% |

* Percent daily value based on a 2,000 calorie diet.

7. Beverage(s)

Beverages suitable for use in the present invention include any beverage that forms an amount of food residue in the digestive tract or that forms an amount of residue which does not impede or adversely affect a predetermined activity or the outcome of such activity. Such beverages may include, but are not limited to, drinks containing natural, e.g., fruit or vegetable, and/or artificial ingredients such as iced tea or coffee, coffee, herbal teas, fruit juices, sports-drinks, dairy-free beverages, sodas, soft drinks and the like. Suitable beverages may also include a blend of various ingredients compounded in dry form which is readily soluble in a fluid, such as water. Such beverages may also comprise a blend of organic ingredients, such as whole herbs, or may include vitamin or herbal enhanced waters in various flavors.

A beverage suitable for use in the present invention includes, but is not limited to, a lemon flavored drink comprising sugar, malic acid, ascorbic acid (vitamin C), aspartame, sodium citrate, natural and artificial flavors, artificial colors (including yellow #5 and #6, red #40, Blue #1) and phenylalanine.

In one alternative embodiment of the present invention, an appropriate serving of a lemon drink may comprise the characteristics listed in Table 18. Additionally, the lemon drink may contain vitamins and/or minerals such that it provides the level of nutrition listed in Table 19.

TABLE 18

Lemon Drink
Nutrition Facts

Serving Size: 1 Packet. (8 fl oz))
Servings Per Container: 1
Amount Per Serving

| Calories 25 | Calories from Fat 0 |
|---|---|
| | % Daily Value* |
| Total Fat 0 g | 0% |
| Sodium 10 mg | 0% |
| Total Carbohydrate 6 g | 2% |
| Sugars 6 g | |
| Protein 0 g | |

*Percent daily value based on a 2,000 calorie diet.

In one alternative embodiment, the food products utilized in the present invention are at least substantially free or completely free of any dairy product or derivative thereof. Also, in another alternative embodiment, the food products utilized in the present invention are at lest substantially free or completely free of any whole wheat product or any product made from whole wheat.

TABLE 19

Vitamins and Minerals

| Vitamin A | 0% |
|---|---|
| Calcium | 0% |

TABLE 19-continued

Vitamins and Minerals

| | |
|---|---|
| Vitamin C | 100% |
| Iron | 0% |

* Percent daily value based on a 2,000 calorie diet.

In one alternative embodiment, the food products utilized in the present invention are at least substantially free or completely free of any dairy product or derivative thereof. Also, in another alternative embodiment, the food products utilized in the present invention are at least substantially free or completely free of any whole wheat product or any product made from whole wheat.

C. Laxative Regimens

To facilitate the removal of food residue from the digestive tract, the dietary regimen of the present invention may be used in conjunction with a laxative regimen. Suitable laxative regimens include, but are not limited to, regimens requiring at least some fluid intake, including, but not limited to, hyperosmotic laxatives, such as the saline, lactulose and polymer types. Other laxative regimens may include the polyethylene glycol (PEG) types. The hyperosmotic and PEG regimens may be used alone or in combination with each other, or in combination with stimulant laxatives (also known as contact laxatives). Stimulant laxatives may be used alone provided they can remove sufficient residue such that a medically and/or diagnostically useful procedure can be performed on the digestive tract.

Saline laxatives suitable for use with the dietary regimen of the present invention may include, but are not limited to, LoSo Prep.™ Magnesium Carbonate, Citric Acid, and Potassium Citrate for Oral Solution, Liqui Prep.™, single or double Fleet.RTM, Visacol.™, Citrate of Magnesia.™, and Haley's M-O.™, all of which are commercially available. Polyethylene glycol laxatives suitable for use in the present invention may include, but are not limited to, Nulytely.™, Colyte.™, Colyte.™ Flavored and Golytely.™, all of which are commercially available.

Stimulant laxatives suitable for use in the present invention include, but are not limited to, LoSo Prep.™ Bisacodyl Tablets, Correctol.RTM, Konsyl.RTM, Dulcolax.RTM, Purge.RTM, Feen-A-Mint.RTM, and Senokot.RTM, all of which are commercially available. Other suitable stimulant laxatives may include bulk-formers, for example, psyllium and polycarbophil, lubricant laxatives such as mineral oil, dehydrochloric acid, stool softeners and/or combinations thereof. In addition, a stimulant laxative in suppository form may be included in the laxative regimen. Such a laxative may include, but is not limited to, Rectolax.™ Suppository, which contains 10 mg of bisacodyl.

An advantage of the present dietary regimen is that it facilitates the efficacy of a laxative regimen such that milder laxative regimens may be used. For example, PEG laxatives, such as Colyte.™ and Golytely.™, may be too strong or harsh for some individuals. This is so because these laxatives require the consumption of a high volume of unpalatable solution containing the cathartic agent over a short period of time. Also, consumption of such large amounts of fluid may induce gagging or vomiting in some individuals. Similarly, some saline laxatives containing sodium phosphate, such as Fleet.RTM, are considered by some individuals as bad-tasting. In contrast, magnesium citrate-based laxatives are considered better tasting than most purgative drinks. Also, magnesium citrate-based laxatives are generally considered more mild because they require the intake of fluid, usually water, over time. A further benefit of magnesium citrate-based laxatives is that they contain a comparably lower sodium content.

Because the dietary regimen of the present invention may facilitate the evacuation of food residue, more milder and better tasting laxative regimens can be substituted for high volume purgative drinks. Thus, a preferred laxative regimen for use in the present invention is the LoSo Prep.™ Bowel Cleansing System (E-Z-EM, Inc. Westbury, N.Y.), which comprises one unit-dose packet of magnesium carbonate, citric acid and potassium citrate for oral solution, four bisacodyl tablets, 5 mg each, one 10 mg bisacodyl suppository, and approximately 80 oz of water or clear liquid for consumption. It is understood that the system, kit, formulation and method of the present invention may or may not require a component or step for removing food residue from the digestive tract. For example, use of the present dietary regimen, with or without a cathartic agent, may be sufficient to adequately prepare the digestive tract for a predetermined activity.

It should be understood that, while the preferred laxative regimen for use in the present invention is the LoSo Prep.™ Bowel Cleansing System, any high volume purgative drink or high sodium cathartic cleansing drink may be used.

Other features of the present invention include improved user compliance and quality of life as compared to conventional techniques for removing food residue from the digestive tract. A problem with conventional techniques is a lack of user-compliance. For example, an individual undertaking the clear-liquid diet may lack the will-power to resist eating solid foods. Also, traditional mechanical preparations such as purgatives may be difficult to complete because they require the user to drink large volumes of fluid. Finally, another problem with the clear liquid diet is that it may not supply adequate levels of nutrition and caloric intake to the individual undertaking the diet, thus causing side-effects such as dizziness and fatigue. As a result, the individual may be unable to complete daily, routine activities while on the diet.

While the level of compliance of any of these procedures depends in part on the motivation and drive of the individual, compliance nevertheless may also be influenced by identifiable and controllable factors such as the ease with which the diet or technique may be utilized, as well as the taste, appearance, and in general, the desirability of the items to be consumed.

The nutritional diet system of the present invention represents an improvement over traditional techniques used to remove residue from the digestive tract. The present invention is designed to facilitate user compliance by providing a variety of solid, semi-solid and liquid food items for consumption. These individual food items are ready to eat or easy to prepare, as well as pleasing in both taste and appearance. Additionally, the present invention is designed to improve the user's quality of life by supplying the user with sufficient caloric intake and nutrition such that daily activities may be undertaken while food residue is substantially removed from the user's digestive tract.

The nutritional dietary system of the present invention comprises one or more food items. Such food items may include, but are not limited to one or more soup products, protein supplements, grain foods, starch foods, fruit or vegetable foods, nutritional drinks or beverages. In an alternative embodiment, the nutritional dietary system of the present invention comprises one or more chicken noodle soups, pastas with stroganoff flavored sauce, chocolate flavored energy bars, cinnamon flavored pears, bananas or apple sauce, vanilla flavored nutritional drinks and one or more lemon drinks.

In another alternative embodiment, the nutritional dietary system of the present invention comprises one or more chicken flavored broths, chicken flavored soups, chocolate protein bars, lemon crisp yogurt covered protein bars, caramel mini-package of potato poppers, cinnamon flavored pears, bananas or apple sauce, vanilla flavored nutritional drinks and one or more lemon drinks.

In another embodiment, the nutritional dietary system of the present invention comprises one or more food items arranged in three separate feedings. The first feeding comprises a nutritional drink, more preferably a vanilla flavored nutritional drink. The second feeding comprises a nutritional drink, a soup product and a beverage, more preferably a vanilla flavored nutritional drink, a chicken noodle soup and a lemon drink. The third feeding comprises a nutritional drink, a grain food and a beverage, more preferably a vanilla flavored nutritional shake, a pasta with stroganoff flavored sauce and a lemon drink. The nutritional dietary system of the present invention may also comprise one or more snacks. Such snacks comprising one or more soup products, grain foods, starch foods, protein supplements, fruit and/or vegetable foods and nutritional drinks, preferably comprising one or more chocolate flavored energy bars, lemon crunch power bars, potato poppers and/or cinnamon flavored pears, bananas or apple sauce.

In another embodiment, the nutritional dietary system of the present invention comprises one or more food items arranged into three specific types of feedings, particularly a breakfast feeding, lunch feeding and a dinner feeding. The breakfast feeding comprises a nutritional drink, more preferably a vanilla flavored nutritional drink. The lunch feeding comprises a nutritional drink, a soup product and a beverage, more preferably a vanilla flavored nutritional drink, a chicken noodle soup and a lemon drink. The dinner feeding comprises a nutritional drink, a grain food and a beverage, more preferably a vanilla flavored nutritional shake, a pasta with stroganoff flavored sauce and a lemon drink. The nutritional dietary system of the present invention may also comprise one or more snacks. Such snacks comprising one or more soup products, grain foods, starch foods, protein supplements, fruit and/or vegetable foods and nutritional drinks, preferably comprising one or more chocolate flavored energy bars, lemon crunch power bars, potato poppers and/or cinnamon flavored pears, bananas or apple sauce.

The nutritional dietary system of the present invention is designed to facilitate user compliance. In one embodiment of the present invention, an individual obtains the system comprising one or more individually prepackaged food items. The system also comprises instructions for coordinating the food items for use together as a single dietary system for removing food residue from the digestive tract. The instructions may be positioned on one or more surfaces of the container holding the food items, or the instructions may be provided on a separate sheet, or any combination thereof. Such instructions may specify the frequency the food items are to be consumed by an individual over time. For example, the instructions may include, for example, instructions to consume a nutritional drink in the morning, consume a nutritional drink, soup product and beverage at mid-day, and to consume a nutritional drink, grain food and beverage in the evening. Additional instructions may include instructions to consume one or more snacks foods between each feeding. Such snack foods may include, but are not limited to, soup products, protein supplements, grain foods, starch foods, fruit and/or vegetable foods and nutritional drinks.

The instructions may also include, for example, instructions for coordinating the dietary regimen for use together with a laxative regimen. For instance certain laxative regimens involve drinking large volumes of clear liquids over a 24-hour period. Thus, the instructions may specify, for example, the amount and type fluids to be consumed over time in conjunction with taking the laxative agent. For example, the instructions may direct the individual to consume at least 32 oz of a clear liquid during the morning and afternoon, at least 16 oz of clear liquid in the evening and at least 16 oz of clear liquid the next morning or prior to a predetermined medical activity, such as surgery or a diagnostic procedure.

The system of the present invention may also provide a container structured to allow for specific placement of the food items and the coordinating instructions. This enables each of the food items to be placed in the kit in the order of their consumption by an individual, thus making the present system easy to follow, which facilitates user compliance. A non-limiting example of such a container is shown in FIG. 1.

In FIG. 1, container (1) contains multiple food items of the present invention. Here, the food items are arranged in the order by which they should be consumed by the individual over about a 20- to 36-hour period. Specifically, nutritional drink (2) is positioned in section (3) located at the front of container (1). A first snack food (4) is positioned in adjacent section (5). Another nutritional drink (6), along with a beverage (7) and soup product (8) is positioned in section (9). A second snack food (15) is positioned in subsequent section (10). In one embodiment of the present invention, the snack food (4) or (15) may comprise a starch food, protein supplement, fruit food or vegetable food. Another nutritional drink (11), beverage (12) and grain food (13) is positioned in the farthest section (14) relative to the front of the container.

Indicia may be included in at least one of the surfaces of the container and/or one or more food items. The indicia may take the form of a writing or illustration or both, to assist the individual to readily distinguish the food items from each other. This feature is especially useful for individuals that are ill, weak or suffer from poor vision, or that experience difficulty in reading labels found on ordinary food containers. In one embodiment of the present invention, the indicia may comprise large lettering or illustrations readily in identifiable colors.

A device for enabling the patient to record consumption of particular food components may also be utilized in the system of the present invention. Such a device may take the form of a "check list" whereby the individual can place a ".check mark." next to the items listed to indicate consumption of such item. In one alternative embodiment, a suitable recordation device (15) is represented in FIG. 2. Providing a recording device further ensures user compliance with the nutritional dietary system of the present invention.

In another embodiment of the present invention, the individual reviews the instructions for coordinating the multiple food items for use as a single nutritional dietary system, and may also review the indicia for distinguishing the food items. The appropriate food items are then selected as indicated by the indicia and/or the instructions, and consumed as instructed by the instructions and/or indicia. Consumption of each food item is then recorded in the recording device (15).

FIG. 10 shows an alternative embodiment wherein the dietary regimen of the present invention is used in conjunction with a laxative regimen. The first feeding (70) is consumed in the morning, for example, at about 8:00 a.m. The first feeding may comprise one nutritional drink or 3 to 5 oz of boiled white rice. The second feeding (72) may be consumed at or about mid-day, for example at 12:00 p.m. Second feeding (72) may comprise one soup product, one nutritional drink and one beverage. After the second feeding, individual drinks (73, 74, 76, 77), each comprising about eight ounces of clear liquid, may be consumed in about one hour intervals. The third feeding (78) may be consumed at about late afternoon or early evening, at about 5:00 p.m., for example. Third feeding (78) may comprise one soup product, one nutritional drink and one beverage. First and second snacks (71, 75) may be consumed between the first and second feeding (70, 72), and second and third feedings (72, 78), respectively. Each snack may comprise one or more protein supplements or starch foods. Such snacks may also comprise a soup product, grain food, fruit or vegetable food. After the third feeding, for example at about 5:30 p.m., a saline laxative (79) is administered. Such laxative may comprise a magnesium-citrate based laxative. A suitable laxative would include, but is not limited to, LoSo Prep.™ Magnesium Carbonate, Citric Acid, and Potassium Citrate for Oral Solution which is a mixture of magnesium carbonate (31%), citric acid (65%), and potassium citrate (3%) dissolved in eight ounces of cold water. After administering the magnesium citrate-based laxative, a drink (80) comprising eight ounces of clear liquid (e.g., water) is consumed, for example at about 6:00 p.m. Subsequently, for example, at about 7:00 p.m., a drink (81) comprising eight ounces of clear liquid (e.g., water) is consumed. A stimulant laxative and drink (82) are administered soon after, for example at about 7:30 p.m. The stimulant laxative may include, but is not limited to, one or more bisacodyl tablets, such as four LoSo Prep.™ bisacodyl (5 mg) tablets. The tablets may be taken with eight ounces of water or any other clear liquid. Subsequently, drink (83) comprising eight ounces of clear liquid (e.g., water) is consumed at about 8:00 p.m., for example. Thereafter, for example at about 9:00 p.m., drink (84) comprising eight ounces of clear liquid (e.g., water) is consumed. No food is consumed afterwards (85). In addition, a suppository may be administered the following morning at least two hours before the predetermined medical activity. A suitable suppository may include, but is not limited to, a suppository comprising about 10 mg of bisacodyl, such as Rectolax.RTM, which is commercially available.

In another embodiment, the present invention is a nutritional dietary kit for use in preparing an individual for a predetermined activity, including but not limited to, an activity requiring a clean digestive tract, particularly the colon. Specifically, the nutritional dietary kit of the present invention comprises one or more food items. Such food items may include, but are not limited to, one or more soup products, protein supplements, grain foods, starch foods, fruit or vegetable foods, nutritional drinks or beverages. In an alternative embodiment, the dietary kit of the present invention comprises one or more chicken noodle soups, pastas with stroganoff flavored sauce, chocolate flavored energy bars, potato poppers, cinnamon flavored pears, bananas or apple sauce, vanilla flavored nutritional drinks and one or more lemon drinks.

In another alternative embodiment, the nutritional dietary kit of the present invention comprises one or more chicken flavored broths, chicken flavored soups, chocolate protein bars, lemon crisp yogurt covered protein bars, caramel mini-package of potato poppers, cinnamon flavored pears, bananas or apple sauce, vanilla flavored nutritional drinks and one or more lemon drinks.

In another embodiment, the nutritional dietary kit of the present invention comprises one or more food items arranged in three separate feedings. The first feeding comprises a nutritional drink, more preferably a vanilla flavored nutritional drink. The second feeding comprises a nutritional drink, a soup product and a beverage, more preferably a vanilla flavored nutritional drink, a chicken noodle soup and a lemon drink. The third feeding comprises a nutritional drink, a grain food and a beverage, more preferably a vanilla flavored nutritional shake, a pasta with stroganoff flavored sauce and a lemon drink. The nutritional dietary kit of the present invention may also comprise one or more snacks. Such snacks comprising one or more soup products, grain foods, starch foods, protein supplements, fruit and/or vegetable foods and nutritional drinks, preferably comprising one or more chocolate flavored energy bars, lemon crunch power bars, potato poppers and/or cinnamon flavored pears, bananas or apple sauce.

In another embodiment, the nutritional dietary kit of the present invention comprises one or more food items arranged into three specific types of feedings, particularly a breakfast feeding, lunch feeding and a dinner feeding. The breakfast feeding comprises a nutritional drink, more preferably a vanilla flavored nutritional drink. The lunch feeding comprises a nutritional drink, a soup product and a beverage, more preferably a vanilla flavored nutritional drink, a chicken noodle soup and a lemon drink. The dinner feeding comprises a nutritional drink, a grain food and a beverage, more preferably a vanilla flavored nutritional shake, a pasta with stroganoff flavored sauce and a lemon drink. The nutritional dietary kit of the present invention may also comprise one or more snacks. Such snacks comprising one or more soup products, grain foods, starch-foods, protein supplements, fruit and/or vegetable foods and nutritional drinks, preferably comprising one or more chocolate flavored energy bars, lemon crunch power bars, potato poppers and/or cinnamon flavored pears, bananas or apple sauce.

The nutritional dietary kit of the present invention is designed to facilitate user compliance. In one embodiment of the present invention, an individual obtains the kit comprising one or more individually prepackaged food items. The kit also comprises instructions for coordinating the food items for use together as a single dietary regimen for removing food residue from the digestive tract. The instructions may be positioned on one or more surfaces of the container holding the food items, or the instructions may be provided on a separate sheet, or any combination thereof. Such instructions may specify the frequency over time the food items are to be consumed. For example, coordinating instructions may include, but are not limited to instructions to consume a nutritional drink in the morning, to consume a nutritional drink, soup product and beverage at midday, and to consume a nutritional drink, grain food and beverage in the evening. Other instructions may include instructions to consume one or more snack foods between feedings.

The nutritional dietary kit of the present invention may also take the form of a container structured to provide specific or general placement of the food components and the instructions. For example, the food items may be placed in the order of their consumption, thus making the present kit easy to use, which facilitates user compliance. A non-limiting example of such a container is shown in FIG. 1.

Indicia may be included on at least one of the surfaces of the container and/or one or more food the items. The indicia may take the form of a writing or illustration or both, to allow the individual to readily distinguish the food items from each other.

A device for enabling the patient to record consumption of particular food items may also be utilized in the nutritional dietary kit of the present invention. Such a device may take the form of a "check list" whereby the patient can place a ".check mark." next to the items listed to indicate consumption of such item. In one alternative embodiment, a suitable recordation device (15) is represented in FIG. 2.

In another embodiment of the nutritional dietary kit of the present invention, the individual reviews the instructions for coordinating the multiple food items for use as a single dietary system, and may also review the indicia for distinguishing the food items. The appropriate food items are then selected as indicated by the instructions and/or indicia, and consumed as instructed by the instructions and/or indicia. Consumption of each food item is then recorded in the recording device (15).

In reference to FIG. 3, a representative kit of the present invention is shown comprising three feedings. A first feeding (16) is placed in one portion of kit (17), a second feeding (18) is placed in an adjoining section of kit (17) and a third feeding (19) is placed in adjoining section of kit (17). Also, two food items, first snack (20) and second snack (21) are placed in an adjacent divided area of the kit (17). In this embodiment, the whole kit comprises approximately 2000 calories.

In FIG. 3, each feeding represents consumption of one or more food items. For example, the first feeding may comprise one nutritional drink (22). The second feeding may comprise one soup product (23), one nutritional drink (24) and one beverage (25). The third feeding may comprise one soup product (26), one nutritional drink (27) and one beverage (28). The first and second snacks (20, 21) may comprise one protein supplement (29) and one starch food (30), respectively. These items may be consumed between the first and second feedings, and second and third feedings, respectively.

Figure 4:
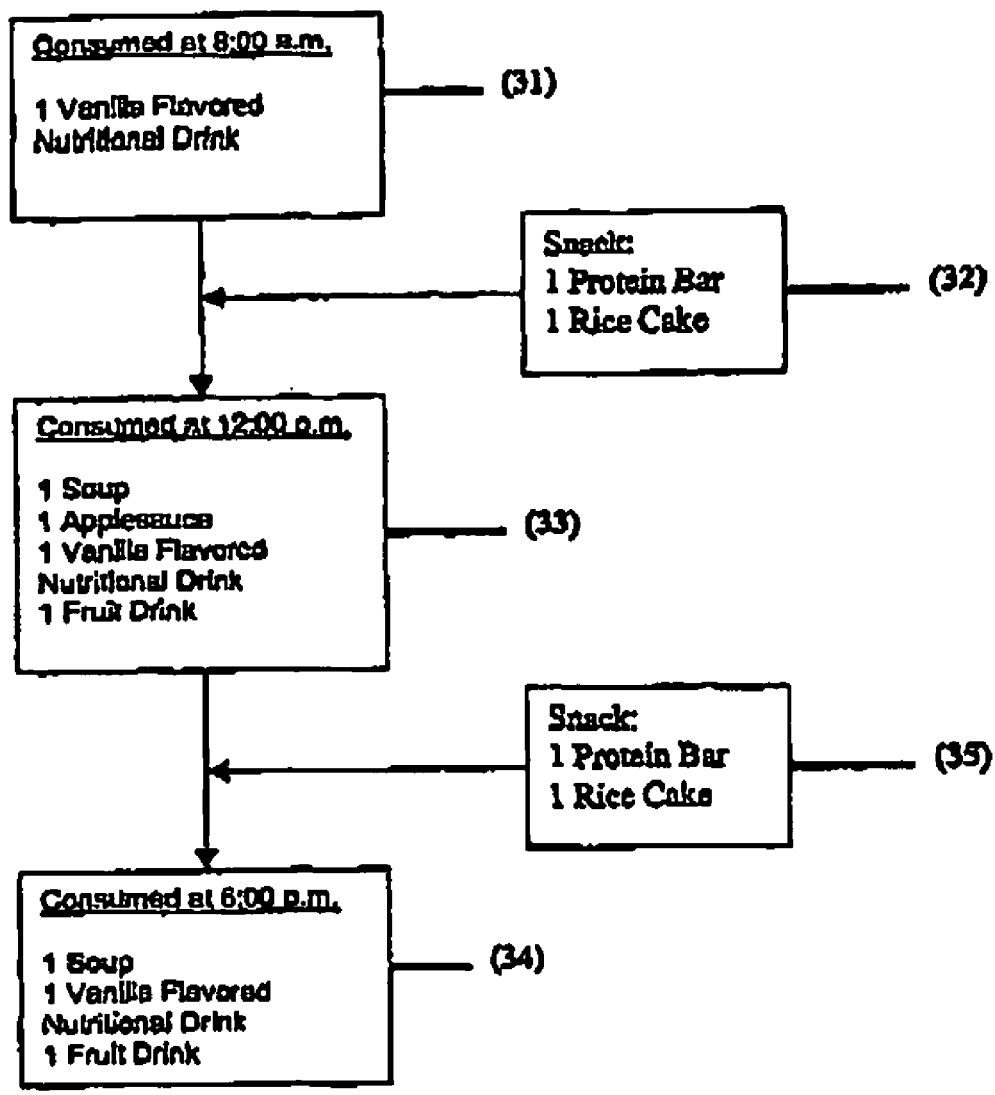
FIG. 4 is a non-limiting diagram of a dietary regimen of the present invention.

In reference to FIG. 4, the kit of the present invention may contain one or more food items arranged into three meals. The first feeding (31) is consumed, for example, at about 8:00 a.m. and may comprise one nutritional drink. A first snack (32) may be provided, and first snack (32) may comprise one protein supplement and/or one starch food. The second feeding (33) may be consumed at about 12:00 p.m. and may comprise one soup product, one nutritional drink, one fruit food and one beverage. The third meal (34) may be consumed at about 6:00 p.m. and may comprise one soup product, one nutritional drink and one beverage. A second snack (35) may be provided, and snack (35) may comprise one protein supplement and/or one starch food. First and second snacks (32, 35) may be consumed between the first and second feeding (31, 33), and second and third feedings (33, 34), respectively.

Figure 5:
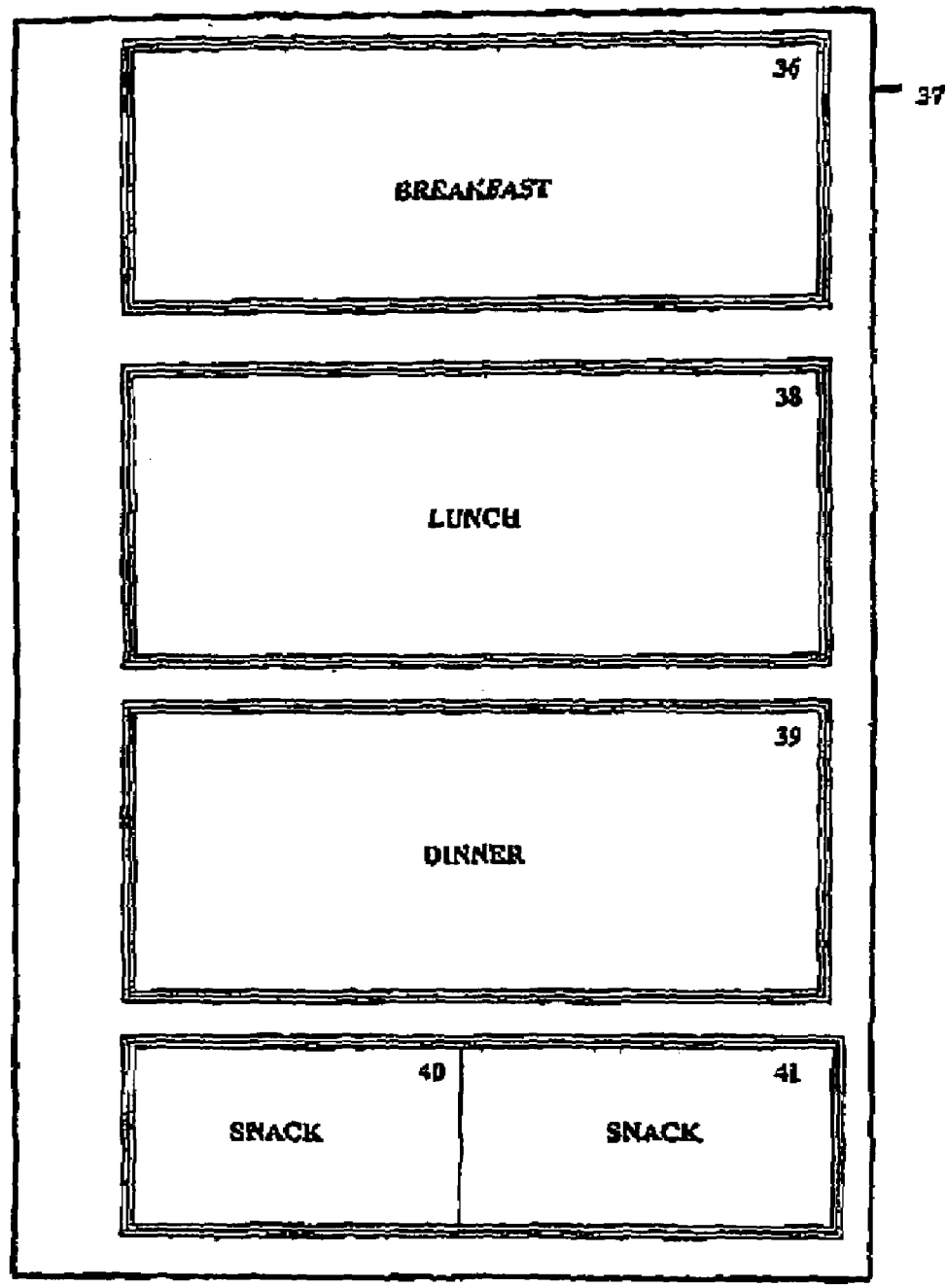
FIG. 5 is a non-limiting example of a kit comprising the food items of the present invention.

Also, the first, second and third feedings (31, 33, 34) may represent a breakfast, lunch and dinner meal, respectively. For example, in reference to FIG. 5, breakfast meal (36) may be placed in one portion of a kit (37), a lunch meal (38) may be placed in an adjoining section of kit (37), a dinner meal (39) may be placed in adjoining section of kit (37) and lastly the two snack items, i.e., first snack (40) and second snack (41), may be placed in an adjacent divided area of kit (37).

In this embodiment, the whole kit comprises approximately 2,000 calories and may be consumed over about a 24-hour period.

In one embodiment of the present invention, the nutritional dietary kit is customizable, i.e., sections of the kit containing one or more food items may be removably interchanged, added or subtracted from the kit to allow for customization of the kit according to particular dietary health concerns or goals. In reference to FIG. 6a, an individual may remove all of the solid food components (43, 44, 48) from kit (42) so that only a kit of liquid food components (45, 46, 47) is provided. In reference to FIG. 6b, an individual may add an additional nutritional drink (49) to kit (42), if extra nutrition is required. In reference to FIG. 6c, the one or more food items of FIG. 6b may be rearranged to reflect a different order of consumption.

Further, if an individual does not want a particular food item(s) in the kit to be consumed, removably subtracting that food item(s) from the kit ensures that it will not be consumed, thus facilitating compliance with the present invention. FIG. 7 shows a non-limiting example of customization of the kit of the present invention by removably adding or subtracting one or more food items from said kit. In FIG. 7, (50) shows an aerial view of a kit of the present invention with one or more individual food items placed therein. (51) shows the kit with individual food items (52) and (53) removed. (54) shows the kit with new food items (55) and (56) added.

Figure 8:
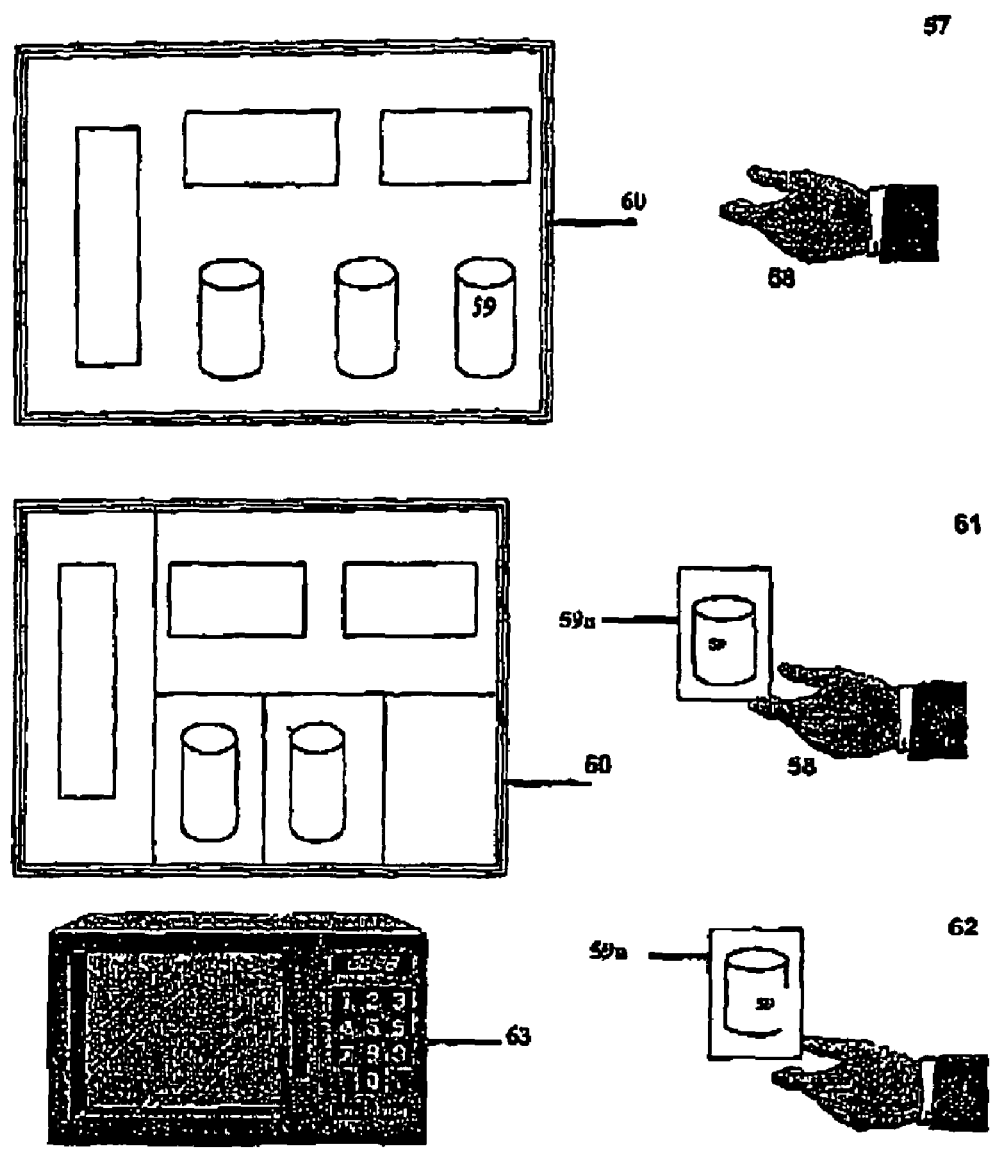
FIG. 8 shows an individual removing a section of a kit comprising the food items of the present invention.

In another embodiment of the present invention, the nutritional dietary kit allows individual sections to be removed in order to prepare a food item for consumption. The individual sections may be attached to the kit separately or in a manner that allows for ready and easy removal from the kit. In reference to FIG. 8, step (57) shows an individual (58) identifying food item (59) in kit (60) for consumption. Step (61) shows the individual (58) removing section (59a) which contains food item (59) from kit (60). Step (62) depicts the individual (58) placing sections (59a) with food item (59) into microwave (63) for cooking.

In another embodiment, the present invention is a method for use in preparing an individual for a predetermined activity, including but not limited to, an activity requiring a clean digestive tract, particularly the colon. Such is accomplished by providing the individual one or more food items for consumption, including, for example, one or more soup products, protein supplements, grain foods, starch foods, fruit or vegetable foods, nutritional drinks or beverages prior to a predetermined activity. The present invention may also be carried out by instructing the individual to obtain the one or more food items, individually or collectively, and consume them. For example, a physician may instruct an individual to prepare, purchase or otherwise obtain the one or more food items, individually or collectively, and instruct the individual to consume said food items prior to a predetermined activity and/or pursuant to dietary regimen.

In an alternative embodiment, the method of the present invention comprises the step of providing one or more chicken noodle soups, pastas with stroganoff flavored sauce, chocolate flavored energy bars, cinnamon pears, bananas or apple sauce, vanilla flavored nutritional drinks and one or more lemon drinks. The method may also comprise the step of instructing the individual to prepare, purchase or otherwise obtain these items, individually or collectively, and consume them pursuant to a predetermined dietary regimen and/or prior to a predetermined activity.

In another alternative embodiment, the method of the present invention comprises the step of providing an individual with one or more chicken flavored broths, chicken flavored soups, chocolate flavored protein bars, lemon crisp yogurt covered protein bars, caramel mini-package of potato poppers, cinnamon flavored pears, bananas or apple sauce, vanilla flavored nutritional drinks and one or more lemon drinks. The method may also comprises the step of instructing the individual to prepare, purchase or otherwise obtain these items, individually or collectively, to consume them pursuant to a predetermined dietary regimen and/or prior to a predetermined activity.

In another embodiment, the method of the present invention comprises the step of providing an individual one or more food items arranged in three separate feedings. The first feeding comprises a nutritional drink, more preferably a vanilla flavored nutritional drink. The second feeding comprises a nutritional drink, a soup product, and a beverage, more preferably a vanilla flavored nutritional drink, a chicken noodle soup and a lemon drink. The third feeding comprises a nutritional shake, a grain food and a beverage, more preferably a vanilla flavored nutritional drink, a pasta with stroganoff flavored sauce and a lemon drink. The method may also comprise the step of instructing the individual to prepare, purchase or otherwise obtain the necessary food items, individually or collectively, to compose these feedings, and consume them pursuant to a predetermined dietary regime and/or prior to a predetermined activity.

In another embodiment, the method of the present invention comprises the step of providing one or more food items arranged into three specific types of feedings, particularly a breakfast feeding, a lunch feeding and a dinner feeding. The breakfast feeding comprises a nutritional drink, more preferably a vanilla flavored nutritional drink. The breakfast feeding may also comprise one or more suitable solid or semi-solid foods, with or without the nutritional drink. The lunch feeding comprises a nutritional drink, a soup product and a beverage, more preferably a vanilla flavored nutritional drink, a chicken noodle soup and a lemon drink. The dinner feeding comprises a nutritional drink, a grain food and a beverage, more preferably a vanilla flavored nutritional drink, a pasta with stroganoff flavored sauce and a lemon drink. The method the present invention may also comprise the step of providing three ounces of chicken, boiled rice, fish or veal to be consumed.

The method of the present invention may also comprise the step of providing one or more snacks. Such snacks may comprise one or more soup products, protein supplements, grain foods, starch foods, fruit or vegetable foods or nutritional drinks, preferably comprising one or more chocolate flavored energy bars, lemon crunch power bars, potato poppers or cinnamon flavored pears, bananas or apple sauce.

Figure 9:
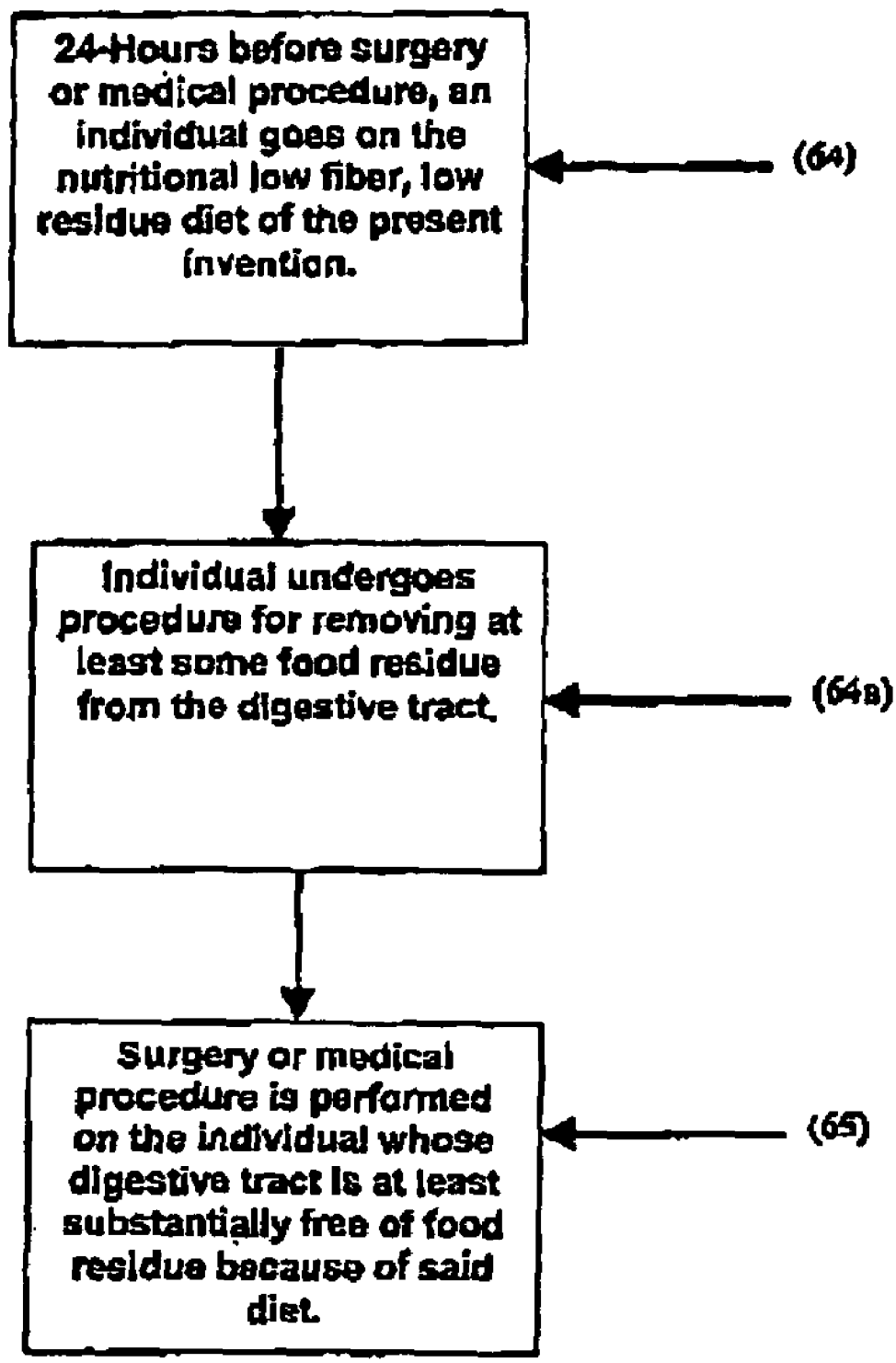
FIG. 9 is a non-limiting diagram of the steps of an alternative embodiment of the present invention.

In reference to FIG. 9, a non-limiting embodiment of the method of the present invention is disclosed. First, step (64) involves having an individual undergo the diet of the present invention approximately twenty-four hours, or one day, before a predetermined activity, including but not limited to, surgery or a diagnostic procedure such as colonoscopy. Step (64a) involves the individual undergoing a procedure for removing food residue from the digestive tract, for example, a laxative regimen. Step (65) involves having the surgery or colonoscopy performed approximately twenty-four hours after step (64). In step (65), the surgery or colonoscopy is successful because sufficient amounts of food residue have been removed from the individual's digestive tract, particularly the colon.

Other predetermined activities may include, but are not limited to, gastrointestinal testing, sigmiodoscopy, barium enema, gastrointestinal surgery, colostomy or ileostomy, or treating an inflammatory condition of the bowel. It is understood that the method of the present invention may or may not include the step of removing food residue from the digestive tract. For example, providing the dietary regimen to the individual, with or without a non cathartic agent, may be sufficient to adequately prepare the digestive tract for a predetermined activity.

Further, in reference to FIG. 9, in step (64) the individual does not experience the detrimental effects that are commonly associated with the clear liquid diet known in the prior art, e.g., symptoms of lightheadedness and dizziness due to insufficient calories and nutrition.

FIG. 3 demonstrates a method for arranging the food items in the order for which they are to be consumed. A first feeding (16) is placed in one portion of kit (17). Next, a second feeding (18) is placed in an adjoining section of kit (17). Then, a third feeding (19) is placed in adjoining section of kit (17). Finally, two snack items, first food item (20) and second food item (21), are placed in an adjacent divided area of the kit (17).

In reference to FIG. 4, a method of consuming the food items of the diet of the present invention is shown. The first feeding (31) is consumed, for example, at about 8:00 a.m. and may comprise one nutritional drink. A first snack (32) may be provided, and first snack (32) may comprise one protein supplement and/or one starch food. The second feeding (33) may be consumed at about 12:00 p.m. and may comprise one soup product, one nutritional drink and one beverage. The third meal (34) may be consumed at about 6:00 p.m. and may comprise one soup product, one nutritional drink and one beverage. A second snack (35) may be provided, and second snack (35) may comprise one protein supplement and/or one starch food. First and second snacks (32, 35) may be consumed between the first and second feeding (31, 33), and second and third feedings (33, 34), respectively.

The present invention is also a method for facilitating user compliance with the dietary system or kit of the present invention. In one embodiment of the present invention, an individual obtains or is provided with a kit or system comprising one or more individually prepackaged food items. The kit or system also comprises instructions for coordinating the food items for use together as a single dietary kit or system for removing food residue from the digestive tract. The instructions may be positioned on one or more surfaces of the container holding the food items, or the instructions may be provided on a separate sheet, or any combination thereof. Such instructions may specify the frequency over time the food items are to be consumed. For example, the instructions may include instructions to consume a nutritional drink in the morning, to consume a nutritional drink, soup product and beverage at midday, and to consume a nutritional drink, grain food and beverage in the evening. Other instructions may include instructions to consume one or more snack foods between feedings.

The method of the present invention may also comprise the step of providing a container structured to provide specific or general placement of one or more food items and coordinating instructions. This enables, for example, the food items to be placed or assembled in the order of their consumption, thus making the present method easy to follow, which facilitates user compliance. In one embodiment, the present method further comprises the steps of arranging the one or more food items in the order by which they should be consumed. A non-limiting example of such a unifying container is shown in FIG. 1.

The method of the present invention may also include the steps of: (1) reviewing the instructions for coordinating the multiple food items for use as a single dietary regimen; (2) reviewing the indicia for distinguishing the food items; (3) selecting the appropriate food items as indicated by the indicia and/or the coordinating instructions; (4) consuming the food items as instructed by the coordinating instructions and/or indicia; and (5) recording consumption of each food item on a recording device.

The method of the present invention may also comprise the step of providing a laxative regimen in order to remove at least some of the food residue from digestive tract, particularly the colon.

In another embodiment, the present invention comprises a nutritional dietary formulation for use in preparing an individual for a predetermined activity, including but, not limited to an activity requiring, a clean digestive tract. Specifically, the formulation comprises one or more food items selected from the group consisting of soup products, protein supplements, grain foods, starch foods, fruit or vegetable foods, nutritional drinks and beverages.

In one embodiment, the present nutritional dietary formulation comprises, one or more food items collectively comprising: from about 0.5 g to about 20 g of dietary fiber; from about 1 g to about 200 g of protein; from about 100 calories to about 3000 calories; and from about 2 g to about 500 g of carbohydrates.

In another embodiment, the nutritional dietary formulation of the present invention comprises one or more food items collectively comprising: from about 1 gram to about 15 g of dietary fiber; from about 10 g to about 150 g of protein; from about 700 calories to about 1800 calories; and from about 100 g to about 400 g of carbohydrates.

In another embodiment, the nutritional dietary formulation of the present invention comprises one or more food items collectively comprising: from about 2 g to about 15 grams of dietary fiber; from about 20 g to about 100 g of protein; from about 900 calories to about 1800 calories; and from about 100 g to about 400 g of carbohydrates.

In another embodiment, the nutritional dietary formulation of the present invention comprises one or more food items collectively comprising, from about 2 g to about 15 grams of dietary fiber; from about 30 g to about 70 g of protein; from about 800 calories to about 2,000 calories; and from about 200 g to about 3,000 g of carbohydrates.

In a preferred embodiment, the nutritional dietary formulation of the present invention comprises one or more food items collectively comprising: at least 100 calories; at least 0.5 g of dietary fiber; at least 0.5% of the calories derived from fat; and about at least 2% by weight of solid material.

In another preferred embodiment, the nutritional dietary formulation of the present invention comprises one or more food items collectively comprising: more than about 600 calories; less than about 15 g of dietary fiber; and less than about 25% of the calories are derived from fat.

Further, in a preferred embodiment, the nutritional dietary formulation of the present invention comprises one or more food items collectively comprising: more than about 600 to about 2,000 calories; from about 0.5 g to about 10 g of dietary fiber; from about 0.5% to about 20% of the calories are derived from fat; and from about 10% to about 30% by weight of solid material.

In another preferred embodiment, the nutritional dietary formulation of the present invention comprises one or more food items collectively comprising: more than about 1,000 to about 1,800 calories; from about 2 g to about 8 g of dietary fiber; from about 10% to about 20% of the calories are derived from fat; and from about 20% to about 30% by weight of solid material.

In the present dietary formulation the one or more food items may constitute a first feeding, a second feeding, and a third feeding. For example, the present dietary formulation may comprise a first feeding which includes at least one nutritional drink, a second feeding which includes at least one nutritional drink, at least one soup product and at least one beverage, a third feeding which includes at least one nutritional drink, at least one grain food and at least one beverage.

The present dietary formulation may also include at least one snack food to be consumed by the individual between one or more feedings. The at least one snack food may be selected from the group consisting of protein supplements, grain foods, starch foods, fruit or vegetable foods.

In another embodiment, the present dietary formulation may comprise a first feeding which includes at least one nutritional drink and at least one beverage, a second feeding which includes at least one soup product and at least one fruit food, a third feeding which includes at least one soup product and at least one beverage and one or more snack foods which includes at least one protein bar and at least one package of potato poppers. In the present nutritional dietary formulation, the predetermined activity may include, but is not limited to, surgery, diagnostic procedures, gastrointestinal testing, colonoscopy, sigmiodoscopy, barium enema, gastrointestinal surgery, colostomy, ileostomy, and treating an inflammatory condition of the bowel, or any other activity requiring at least some removal of food residue form the digestive tract, particularly the colon and bowel.

In another alternative embodiment, the present invention may provide at least one food product that requires at least some mastication in order to be consumed by an individual. Such food product may include, but is not limited to, any of the solid or semi-solid food products described herein. In practice, for example, the individual may be provided at least one solid food product requiring mastication. The act of mastication, it is believed, contributes to an the individual's sense of well being while preparing for the predetermined activity. For example, it is believed that the process of mastication may help an individual feel more replete or satiated, thus resulting in higher user satisfaction and compliance with the present dietary regimen. Further, because the dietary regimen of the present invention may require at least some mastication, it is an improvement over traditional clear liquid diets because, typically, consumption of the clear liquid diet requires no mastication.

In another alternative embodiment, the food products utilized in the present invention may include one or more foods ordinarily consumed in Western cultures, such as for example, North America. As such, the foods are more appealing to Westerners, thus resulting in higher user satisfaction and compliance by those individuals. Western type foods suitable for the present invention include any food product associated with a Western diet and that forms no food residue which does not impede or adversely affect a predetermined activity or the outcome of such activity. Such foods include, but are not limited to, any suitable soup product, protein supplements, grain foods, nutritional drinks, fruit or vegetable foods, or beverages such as those described herein.

EXAMPLES

The invention may be further understood by a consideration of the following examples, which are intended to be purely exemplary of the use of the invention.

Example 1

Table 20 is illustrative of a dietary system and/or kit of the present invention.

ing in a higher than desired frequency of repeating the procedure because retained food residue, such as fecal debris, adversely affects the physician's ability to properly perform the procedure.

A study is described below wherein one objective sought to compare the adequacy of using the dietary regimen of the present invention in conjunction with a laxative regimen. In this study, adequacy of food residue removal was defined as

TABLE 20

| | Vanilla Drink | Chicken Noodle Soup | Chicken Broth | Pears, bananas or apple sauce | Chocolate Power Bar | Lemon Crunch Power Bar | Caramel Package of potato poppers | Tropical Fruit Drink | Total - Kit with Solid Foods | Total - Kit without Solid Foods |
|---|---|---|---|---|---|---|---|---|---|---|
| Calories | 250 | 100 | 5 | 50 | 160 | 160 | 100 | 25 | 1375 | 955 |
| Calories From Fat | 50 | 15 | 0 | 0 | 35 | 45 | 0 | 0 | 245 | 165 |
| Percent Fat Calories | N/A | N/A | N/A | N/A | N/A | N/A | N/A | N/A | 18% | 17% |
| Total Fat (g) | 5.5 | 2 | 0 | 0 | 4 | 5 | 0 | 0 | 27.5 | 18.5 |
| Saturated Fat (g) | 0.5 | 0 | 0 | 0 | 2 | 2.5 | 0 | 0 | 6 | 1.5 |
| Cholesterol (mg) | 10 | 25 | 0 | 0 | 0 | 0 | 0 | 0 | 55 | 55 |
| Sodium (mg) | 50 | 750 | 910 | 30 | 100 | 140 | 20 | 10 | 2120 | 1860 |
| Potassium (mg) | 100 | 0 | 0 | 0 | 70 | 20 | 0 | 0 | 390 | 300 |
| Total Carbohydrate (g) | 41 | 16 | 1 | 13 | 16 | 16 | 22 | 6 | 219 | 165 |
| Dietary Fiber (g) | 0 | 0 | 0 | 2 | 0 | 0 | 0 | 0 | 2 | 2 |
| Sugars (g) | 26 | 2 | 1 | 11 | 7 | 8 | 6 | 6 | 125 | 104 |
| Protein (g) | 9 | 6 | 0 | 0 | 15 | 15 | 0 | 0 | 63 | 33 |
| Quantity-Kit | 3 | 1 | 1 | 1 | 1 | 1 | 1 | 2 | N/A | N/A |

Example 2

Table 21 is illustrative of a dietary system and/or kit of the present invention.

the ability to perform a diagnostically useful colonoscopy procedure. Another objective of the study sought to compare patient acceptance of and compliance to the diet/laxative regimens. Patient acceptance and compliance was defined as

TABLE 21

| | Vanilla Drink | Chicken Noodle Soup | Pasta Stroganoff | Pears, bananas or apple sauce | Chocolate Power Bar | Potato Poppers | Lemon Drink | Total - Kit with Solid Foods |
|---|---|---|---|---|---|---|---|---|
| Calories | 240 | 100 | 140 | 100 | 170 | 98 | 25 | 1.548 |
| Calories From Fat | 35 | 20 | 30 | 0 | 45 | 10 | 0 | 255 |
| Percent Fat Calories | N/A | N/A | N/A | N/A | N/A | N/A | N/A | 16% |
| Total Fat (g) | 4 | 2.5 | 3 | 0 | 5 | 1 | 0 | 28.5 |
| Saturated Fat (g) | 0 | 0.5 | 2 | 0 | 3.5 | 0 | 0 | 9.5 |
| Cholesterol (mg) | 0 | 0 | 10 | 0 | 0 | 0 | 0 | 10 |
| Sodium (mg) | 150 | 650 | 490 | 15 | 125 | 168 | 10 | 2043 |
| Potassium (mg) | 100 | 150 | 160 | 0 | 190 | 0 | 0 | 990 |
| Total Carbohydrate (g) | 41 | 18 | 24 | 23 | 24 | 10 | 6 | 258 |
| Dietary Fiber (g) | 0 | 0 | 0 | 1 | 1 | 0 | 0 | 3 |
| Sugars (g) | 26 | 5 | 4 | 21 | 15 | 0 | 6 | 150 |
| Protein (g) | 9 | 2 | 5 | 0 | 10 | 1 | 0 | 55 |
| Quantity in Kit | 3 | 1 | 1 | 1 | 2 | 1 | 2 | N/A |

Example 3

Patient preparation for endoscopy of the digestive tract requires at least some removal of food residue from the digestive tract, particularly the colon. The inability of patients to adequately comply with customary preparatory instructions, specifically with regard to the diet, has resulted in performing endoscopy on a poorly cleansed colon, resultsatiety from the diet, absence of complaints and an absence of adverse events related to the colon preparation procedure.

Study Protocol

The study was a single blind, randomized and controlled evaluation of three groups of subjects who were scheduled to undergo a routine colonoscopy. A total of 36 subjects participated in the study.

The subjects were divided into three groups, one control group and two active groups, which are described in Table 22.

TABLE 22

|  | Control Group #1 | Active Group #2 | Active Group #3 |
|---|---|---|---|
| Diet | Clear liquid diet | Patients in this group were given the dietary regimen described in Table 20. | Patients in this group were given the dietary regimen described in Table 20, which contained liquid foods only. |
| Laxation | Patients in this group underwent laxative treatment on the evening prior to their scheduled procedure. The laxative treatment consisted of two 45 mL doses of Fleet ® Phospho-soda followed by continual hydration until retiring for the evening. | Patients underwent laxation using a saline/contact laxative regimen, namely LoSo Prep ™ Bowel Cleansing System, followed by continual hydration until retiring for the evening. | Patients underwent laxation using a saline/contact laxative regimen, namely LoSo Prep ™ Bowel Cleansing System, followed by continual hydration until retiring for the evening. |

At the time of enrolling in the study, each subject was randomly assigned to a study group and received both written and verbal instruction for their specific diet and laxative regimen. Subjects were also scheduled for their colonoscopy exam, and instructed on when to begin their bowel preparation.

Subjects in Control Group #1 did not begin their bowel preparation until the day before the scheduled exam. Subjects in Active Groups #2 and #3 began their preparations two days before their scheduled exam. Specifically, two days before the exam, the subjects in the Active Groups were instructed to eat only certain foods for lunch and dinner. These subjects were given a list of allowable and not-allowable foods for consumption. For example, allowable foods included white (refined) breads, Saltine crackers and cooked rice, and unallowable foods included whole grain breads, corn crackers and cereals, and popcorn. A complete list of the allowed and non-allowable foods provided to Active Groups #2 and #3 is shown in FIGS. 14, 16-17.

Subjects from each group were instructed to consume specific foods the day before their scheduled exam. Subjects in Control Group #1 were instructed to consume only clear liquids, including liquids such as apple juice, Jell-O, white grape juice, bouillon, coffee and tea. Further, these subjects were instructed not to consume any dairy products, carbonated drinks, red Jell-O or juices with pulp. Subjects in this group were also instructed to drink lots of fluids. Further, they were instructed to consume a mixture of 1 1/2 oz. of Fleet.™ Phospho-Soda in 4 oz. of water at 4 p.m. and 8 p.m. A list of the written instructions provided to Control Group #1 is shown in FIG. 11.

Subjects in Active Groups #2 and #3 were provided Kit A and Kit B, respectively. Each kit contained the dietary regimen of the present invention. The contents of Kits A and B are shown in FIGS. 12 and 13, respectively. The content of each kit is also shown in Table 20, with "Kit With Solid Foods" representing Kit A, and "Kit Without Solid Foods" representing Kit B. The dietary regimen and laxative system used for each kit is shown in FIGS. 16-19. Subjects in the Active Groups were instructed to consume only those food items in their kit on the day before their scheduled exam. These patients were also asked to document which items they had consumed at each meal by marking the names of the items they had eaten with a check mark. Subjects in the Active Groups were also instructed to drink at least two quarts of water between the hours of 1:00 p.m. and 10:00 p.m. on the day before the exam. At approximately 5:30 p.m. on the day before the exam, the Active Group subjects were instructed to consume a magnesium citrate based laxative in water (LoSo Prep.™ Magnesium Carbonate, Citric Acid, and Potassium Cititrale for Oral Solution). At approximately 7:30 p.m. on the same day, the subjects were instructed to take four bisacodyl tablets (5 mg each).

After all of the subjects completed their laxative regimens, a colonoscopy was performed on each one. On the day of the exam, Active Groups #2 and #3 were instructed to use a bisacodyl suppository (10 mg) at least approximately one to two hours prior to their exam. Also prior to each exam, each subject was asked questions about their preparation regimen.

Study Results

The results of the study are shown in Table 23, below.

TABLE 23

| Results: | Control Group #1 | Active Group #2 | Active Group #3 |
|---|---|---|---|
| Overall preparation rated "excellent" | 33.3% | 66.7% | 66.7% |
| Significant amounts of retained stool noted at colonoscopy | 50% | 25% | 25% |
| The preparation was rated "intolerable" to "very intolerable" | 8.3% | 0% | 0% |
| The preparation was rated "tolerable" to "very tolerable" | 91.7% | 100% | 100% |
| Adequate visualization of the colon was obtained | 100% | 100% | 100% |
| Patients would use the same preparation again | 75% | 75% | 66.7% |

As shown in Table 23, the dietary regimen of the present invention, when combined with a laxative regimen, was rated "more tolerable" as compared to a standard colon cleansing preparation, such as Fleet.™ Phospho-Soda and clear liquid diet. Also, using the present dietary regimen with a laxative regimen resulted in an adequate colon examination and better overall colon cleansing experience as compared to the standard colon preparation regimen. This is an unexpected result in view of the prior art, which has advocated only a clear liquid diet with a separate high-volume purgative or high sodium cathartic cleansing for preparation of the colon.

While the above embodiments are disclosed in detail, it is not meant to limit the scope of the claimed invention. Indeed, it will be appreciated by those skilled in the art that various changes and modifications to the subject invention can be made without departing from the spirit and scope of the invention. For example, one skilled in the art would recognize that the present invention encompasses variations of the embodiments discussed herein. Therefore, different food products may be substituted for the specific food products described herein and the layout of the kit may be modified. Also, food items may be substituted among and between each other.

The figures and attachments herein are presented for illustrative purpose only. They are not intended to limit the scoped of the invention. Further, it should be understood that various changes and modifications to the presently preferred embodiments described herein will be apparent to those skilled in the art. Such changes and modification can be made without departing from the spirit and scope of the present invention and without diminishing its advantages. It is therefore intended that such changes and modification be covered by the appended claims.

Also the invention may suitably comprise, consist of or consist essentially of the elements described herein. Further, the invention described herein suitably may be practiced in the absence of any element which is not specifically disclosed herein.

I claim:

1. A kit for preparing an individual's digestive tract for a gastrointestinal procedure, the kit comprising multiple, separate food items including: (a) at least one solid food item selected from the group consisting of soup products, protein supplements, grain foods, starch foods, and fruit or vegetable foods, and (b) at least one nutritional drink; wherein the multiple food items collectively comprise:
   i. from about 600 to about 2,000 calories;
   ii. from about 0.5 grams to about 10 grams of dietary fiber;
   iii. from about 0.5% to about 20% of the calories are derived from fat; and
   iv. from about 10% to about 30% by weight of solid material;
   and further comprising a laxative suitable for administration prior to the gastrointestinal procedure, wherein the kit is suitable for use in preparing the individual such that the gastrointestinal procedure can be performed on the individual's digestive tract without requiring the individual to undergo a diet consisting only of liquids over a 20 to 36 hour period prior to the gastrointestinal procedure.

2. The kit of claim 1, wherein the multiple food items collectively comprise,
   i. from about 1,000 to about 1,800 calories;
   ii. from about 2 grams to about 8 grams of dietary fiber;
   iii. from about 10% to about 20% of the calories are derived from fat; and
   iv. from about 20% to about 30% by weight of solid material.

3. The kit of claim 1, wherein the soup products are selected from the group consisting of flavored bouillon, strained soup, vegetable soup, soup containing beef, poultry, fish or veal, soup with legumes, chicken flavored broth, chicken noodle soup, and chicken and rice soup.

4. The kit of claim 1, wherein the protein supplements are selected from the group consisting of protein bars, energy bars, nutrition bars, sports bars, and baked goods.

5. The kit of claim 1, wherein the starch foods are selected from the group consisting of pasta, boiled rice, finely-milled wheat or cornbread, soda cracker, tapioca pudding, refined cooked cereal, yam, light white rye without seeds, roll without seeds, biscuit, pancake, sweet potato without skin, and grits.

6. The kit of claim 1, wherein the fruit foods are selected from the group consisting of pears, bananas or apple sauce, fruit ice, fruit puree, fruit juices without pulp, and canned fruits.

7. The kit of claim 1, wherein the multiple food items further comprise at least one item selected from the group consisting of meats, poultry, fish, and veal.

8. The kit of claim 1, further comprising instructions for coordinating the multiple food items for use together as a dietary regimen.

9. The kit of claim 1, further comprising a device for recording the consumption of the multiple food items by the individual.

10. The kit of claim 8, wherein the instructions specify that the multiple food items are to be consumed by the individual over a 20 to 36 hour period prior to the gastrointestinal procedure.

11. The kit of claim 1, wherein the multiple food items are contained in a single package or carton.

12. The kit of claim 1, wherein the multiple, separate food items are separately housed within the kit.

13. The kit of claim 1, wherein the grain foods are selected from the group consisting of soy, cereal, cereal bars, and bread.

14. The kit of claim 1, wherein the multiple food items are packaged in a form identifiable as separate first, second, and third feedings.

15. The kit of claim 14, wherein the first feeding comprises a nutritional drink.

16. The kit of claim 14, wherein the second feeding comprises a nutritional drink, a soup product, and a beverage.

17. The kit of claim 14, wherein the third feeding comprises a nutritional drink, a grain food, and a beverage.

18. The kit of claim 14, wherein the multiple food items further comprise one or more snack feedings.

* * * * *